US012710262B2

(12) United States Patent
Cheng et al.

(10) Patent No.: US 12,710,262 B2
(45) Date of Patent: Aug. 18, 2026

(54) BOND-SELECTIVE FULL-FIELD OPTICAL COHERENCE TOMOGRAPHY

(71) Applicant: Trustees of Boston University, Boston, MA (US)

(72) Inventors: Ji-Xin Cheng, Newton, MA (US); Haonan Zong, Brighton, MA (US); Celalettin Yurdakul, Santa Clara, CA (US); M. Selim Ünlü, Newton Highlands, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 18/761,623

(22) Filed: Jul. 2, 2024

(65) Prior Publication Data

US 2025/0012557 A1 Jan. 9, 2025

Related U.S. Application Data

(60) Provisional application No. 63/525,461, filed on Jul. 7, 2023.

(51) Int. Cl.
*G01B 9/02091* (2022.01)
*A61B 5/00* (2006.01)
(Continued)

(52) U.S. Cl.
CPC ........ *G01B 9/02091* (2013.01); *A61B 5/0066* (2013.01); *A61B 5/0073* (2013.01);
(Continued)

(58) Field of Classification Search
CPC ............ G01B 9/02091; G01B 9/02041; G01B 9/02063; A61B 5/0066; A61B 5/0073;
(Continued)

(56) References Cited

U.S. PATENT DOCUMENTS 8,559,016 B2 * 10/2013 Nebosis ............ G01B 9/02087 356/497
9,593,935 B2 * 3/2017 Osawa .............. G01B 9/02091
(Continued)

FOREIGN PATENT DOCUMENTS

CN 108931478 A * 12/2018 ............ G01N 21/21
CN 109984731 A * 7/2019 .......... A61B 3/1233
(Continued)

OTHER PUBLICATIONS

Zhang, Delong, et al. “Depth-resolved mid-infrared photothermal imaging of living cells and organisms with submicrometer spatial resolution.” Science advances 2.9 (2016): e1600521. (Year: 2016).*
(Continued)

*Primary Examiner* — Michelle M Iacoletti
*Assistant Examiner* — Noah J. Haney
(74) *Attorney, Agent, or Firm* — Cesari and McKenna, LLP; Steven M. Mills

(57) ABSTRACT

A wide-field bond-selective optical coherence tomography (OCT) system and method for imaging a sample includes generating infrared light and directing the infrared light onto the sample to selectively heat the sample. Probe light is also directed onto the sample. A first actuator provides sample depth scanning with respect to a first objective in a reference arm of the system, and a second actuator provides sample depth scanning with respect to a second objective in a sample arm of the system. A detection system receives scattered probe light reflected from the sample. A change in the received probe light from the sample that is indicative of absorption of infrared light.

28 Claims, 14 Drawing Sheets

(51) Int. Cl.

| | |
|---|---|
| ***G01B 9/02*** | (2022.01) |
| ***G01B 9/02055*** | (2022.01) |
| ***G01N 21/17*** | (2006.01) |
| ***G01N 21/47*** | (2006.01) |
| ***G01N 21/63*** | (2006.01) |
| ***G02B 21/00*** | (2006.01) |

(52) U.S. Cl.
CPC ..... *G01B 9/02041* (2013.01); *G01N 21/4795* (2013.01); *G01N 21/636* (2013.01); *G01B 9/02063* (2013.01); *G01N 2021/1714* (2013.01); *G01N 2223/6126* (2013.01); *G02B 21/0056* (2013.01)

(58) Field of Classification Search
CPC ......... G01N 21/636; G01N 2021/1714; G01N 2223/6126; G02B 21/0056
USPC .......................................................... 356/497
See application file for complete search history.

(56) References Cited

U.S. PATENT DOCUMENTS

| | | | | |
|---|---|---|---|---|
| 10,317,656 B2 * | 6/2019 | Dubois | G02B 21/0056 | |
| 2010/0157308 A1 * | 6/2010 | Xie | G01B 9/0205 | 356/477 |
| 2013/0134310 A1 * | 5/2013 | Furstenberg | G01J 3/443 | 250/353 |
| 2013/0182096 A1 * | 7/2013 | Boccara | G02B 21/16 | 348/79 |
| 2015/0223681 A1 * | 8/2015 | Kuranov | A61B 5/0066 | 356/479 |
| 2016/0018327 A1 * | 1/2016 | Hogan | A61B 5/0075 | 356/479 |
| 2016/0278629 A1 * | 9/2016 | Schuele | A61B 3/1225 | |
| 2017/0276920 A1 * | 9/2017 | Frankel | G02B 21/0048 | |
| 2019/0298167 A1 * | 10/2019 | Lapierre-Landry | A61B 3/102 | |
| 2020/0025677 A1 * | 1/2020 | Prater | G01N 21/65 | |
| 2020/0217643 A1 * | 7/2020 | Schnell | G01N 21/4788 | |
| 2020/0271436 A1 * | 8/2020 | Ho | G01B 9/02037 | |
| 2021/0164894 A1 * | 6/2021 | Prater | G01N 21/35 | |
| 2021/0345873 A1 * | 11/2021 | Mazlin | G01B 9/02077 | |
| 2022/0326148 A1 * | 10/2022 | Bhargava | G01N 21/3563 | |

FOREIGN PATENT DOCUMENTS

| | | | |
|---|---|---|---|
| CN | 111829985 A * | 10/2020 | G01N 21/45 |
| CN | 112268505 A * | 1/2021 | G01B 11/2441 |

OTHER PUBLICATIONS

Nahas, Amir, et al. "Detection of plasmonic nanoparticles with full field-OCT: optical and photothermal detection." Biomedical optics express 5.10 (2014): 3541-3546. (Year: 2014).*

Ravichandran, Naresh Kumar, et al. "Label-free photothermal optical coherence microscopy to locate desired regions of interest in multiphoton imaging of volumetric specimens." Scientific Reports 13.1 (2023): 3625. (Year: 2023).*

International Search Report and Written Opinion mailed Sep. 13, 2024 for International Patent Application PCT/US2024/036514 filed Jul. 2, 2024 for Trustees of Boston University, 14 pages.

Huang, D., et al., Optical Coherence Tomography. Science, 1991. 254(5035): p. 1178-1181.

Fercher, A.F., et al., Measurement of intraocular distances by backscattering spectral interferometry. Optics communications, 1995. 117(1-2): p. 43-48.

Wojtkowski, M., et al., In vivo human retinal imaging by Fourier domain optical coherence tomography. Journal of biomedical optics, 2002. 7(3): p. 457-463.

Nassif, N., et al., In vivo human retinal imaging by ultrahigh-speed spectral domain optical coherence tomography. Optics letters, 2004. 29(5): p. 480-482.

Beaurepaire, E., et al., Full-field optical coherence microscopy. Optics letters, 1998. 23(4): p. 244-246.

Mazlin, V., et al., In vivo high resolution human corneal imaging using full-field optical coherence tomography. Biomedical optics express, 2018. 9(2): p. 557-568.

Mecê, P., et al., High-resolution in-vivo human retinal imaging using full-field OCT with optical stabilization of axial motion. Biomedical optics express, 2020. 11(1): p. 492-504.

Durkin, J.R., et al., Imaging of Mohs micrographic surgery sections using full-field optical coherence tomography: a pilot study. Dermatologic surgery, 2014. 40(3): p. 266-274.

Assayag, O., et al., Large field, high resolution full-field optical coherence tomography: a pre-clinical study of human breast tissue and cancer assessment. Technology in cancer research & treatment, 2014. 13(5): p. 455-468.

Jain, M., et al., Modified full-field optical coherence tomography: A novel tool for rapid histology of tissues. Journal of pathology informatics, 2011. 2(1): p. 28.

Cheng, J.-X. and X.S. Xie, Vibrational spectroscopic imaging of living systems: An emerging platform for biology and medicine. Science, 2015. 350(6264): p. aaa8870.

Freudiger, C.W., et al., Label-free biomedical imaging with high sensitivity by stimulated Raman scattering microscopy. Science, 2008. 322(5909): p. 1857-1861.

Hu, F., L. Shi, and W. Min, Biological imaging of chemical bonds by stimulated Raman scattering microscopy. Nature methods, 2019. 16(9): p. 830-842.

Levin, I.W. and R. Bhargava, Fourier transform infrared vibrational spectroscopic imaging: integrating microscopy and molecular recognition. Annual review of physical chemistry, 2005. 56: p. 429.

Baker, M.J., et al., Using Fourier transform IR spectroscopy to analyze biological materials. Nature protocols, 2014. 9 (8): p. 1771-1791.

Zhang, D., et al., Depth-resolved mid-infrared photothermal imaging of living cells and organisms with submicrometer spatial resolution. Science Advances, 2016. 2(9): p. e1600521.

Li, Z., et al., Super-Resolution Far-Field Infrared Imaging by Photothermal Heterodyne Imaging. The Journal of Physical Chemistry B, 2017. 121(37): p. 8838-8846.

Li, C., et al., Mid-Infrared Photothermal Imaging of Active Pharmaceutical Ingredients at Submicrometer Spatial Resolution. Analytical Chemistry, 2017. 89(9): p. 4863-4867.

Li, X., et al., Fingerprinting a Living Cell by Raman Integrated Mid-Infrared Photothermal Microscopy. Analytical Chemistry, 2019. 91(16): p. 10750-10756.

Samolis, P.D. and M.Y. Sander, Phase-sensitive lock-in detection for highcontrast mid-infrared photothermal imaging with sub-diffraction limited resolution. Optics Express, 2019. 27(3): p. 2643-2655.

Pavlovetc, I.M., et al., Approaches to mid-infrared, super-resolution imaging and spectroscopy. Physical Chemistry Chemical Physics, 2020. 22(8): p. 4313-4325.

Yin, J., et al., Nanosecond-resolution photothermal dynamic imaging via MHZ digitization and match filtering. Nature Communications, 2021. 12(1): p. 1-11.

Zhang, Y., et al., Vibrational Spectroscopic Detection of a Single Virus by Mid-Infrared Photothermal Microscopy. Analytical Chemistry, 2021. 93(8): p. 4100-4107.

Bai, Y., et al., Ultrafast chemical imaging by widefield photothermal sensing of infrared absorption. Science Advances, 2019. 5(7): p. eaav7127.

Tamamitsu, M., et al., Quantitative phase imaging with molecular vibrational sensitivity. Optics Letters, 2019. 44(15): p. 3729-3732.

Toda, K., et al., Molecular contrast on phase-contrast microscope. Scientific Reports, 2019. 9(1): p. 9957.

Zhang, D., et al., Bond-selective transient phase imaging via sensing of the infrared photothermal effect. Light: Science & Applications, 2019. 8(1): p. 116.

Schnell, M., et al., All-digital histopathology by infrared-optical hybrid microscopy. Proceedings of the National Academy of Sciences, 2020. 117(7): p. 3388.

(56) References Cited

OTHER PUBLICATIONS

Tamamitsu, M., et al., Label-free biochemical quantitative phase imaging with mid-infrared photothermal effect. Optica, 2020. 7(4): p. 359-366.

Toda, K., M. Tamamitsu, and T. Ideguchi, Adaptive dynamic range shift (ADRIFT) quantitative phase imaging. Light: Science & Applications, 2021. 10(1): p. 1.

Yurdakul, C., et al., Bond-selective interferometric scattering microscopy. Journal of Physics D: Applied Physics, 2021. 54(36): p. 364002.

Zhang, Y., et al., Fluorescence-Detected Mid-Infrared Photothermal Microscopy. Journal of the American Chemical Society, 2021.

Zong, H., et al., Background-suppressed high-throughput mid-infrared photothermal microscopy via pupil engineering. ACS Photonics, 2021. 8(11): p. 3323-3336.

Zhao, J., et al., Bond-selective intensity diffraction tomography. Nature Communications, 2022. 13(1): p. 7767.

Bai, Y., J. Yin, and J .- X. Cheng, Bond-selective imaging by optically sensing the mid-infrared photothermal effect. Science Advances, 2021. 7(20): p. eabg1559.

Xia, Q., et al., Mid-Infrared Photothermal Microscopy: Principle, Instrumentation, and Applications. The Journal of Physical Chemistry B, 2022. 126(43): p. 8597-8613.

Adler, D.C., et al., Photothermal detection of gold nanoparticles using phasesensitive optical coherence tomography. Optics express, 2008. 16(7): p. 4376-4393.

Lapierre-Landry, M., et al., In vivo photothermal optical coherence tomography of endogenous and exogenous contrast agents in the eye. Scientific reports, 2017. 7(1): p. 1-9.

Lapierre-Landry, M., et al., Imaging melanin distribution in the zebrafish retina using photothermal optical coherence tomography. Translational vision science & technology, 2018. 7(5): p. 4-4.

Goetz, G., et al., Interferometric mapping of material properties using thermal perturbation. Proceedings of the National Academy of Sciences, 2018. 115(11): p. E2499-E2508.

Skala, M.C., et al., Photothermal optical coherence tomography of epidermalgrowth factor receptor in live cells using immunotargeted gold nanospheres. Nano letters, 2008. 8(10): p. 3461-3467.

Paranjape, A.S., et al., Depth resolved photothermal OCT detection ofmacrophages in tissue using nanorose. Biomedical Optics Express, 2010. 1(1): p. 2-16.

Zhou, C., et al., Photothermal optical coherence tomography in ex vivo humanbreast tissues using gold nanoshells. Optics letters, 2010. 35(5): p. 700-702.

Jung, Y., et al., Three-dimensional high-resolution imaging of gold nanorodsuptake in sentinel lymph nodes. Nano letters, 2011. 11(7): p. 2938-2943.

Tucker-Schwartz, J.M., et al., Dual-modality photothermal optical coherence tomography and magnetic-resonance imaging of carbon nanotubes. Optics letters, 2012. 37(5): p. 872-874.

Lapierre-Landry, M., et al., Photothermal optical coherence tomography of indocyanine green in ex vivo eyes. Optics letters, 2018. 43(11): p. 2470-2473.

Zorin, I., et al., Dual-band infrared optical coherence tomography using a single supercontinuum source. Optics Express, 2020. 28(6): p. 7858-7874.

Potma, E.O., et al., Rapid chemically selective 3D imaging in the mid-infrared. Optica, 2021. 8(7): p. 995-1002.

DeFlores, L.P. and A. Tokmakoff, Water Penetration into Protein Secondary Structure Revealed by Hydrogen- Deuterium Exchange Two-Dimensional Infrared Spectroscopy. Journal of the American Chemical Society, 2006. 128(51): p. 16520-16521.

Cakmak, G., et al., Amifostine, a radioprotectant agent, protects rat brain tissue lipids against ionizing radiation induced damage: an FTIR microspectroscopic imaging study. Archives of biochemistry and biophysics, 2012. 520(2): p. 67-73.

Apelian, C., et al., Dynamic full field optical coherence tomography: subcellular metabolic contrast revealed in tissues by interferometric signals temporal analysis. Biomedical optics express, 2016. 7(4): p. 1511-1524.

Mazlin, V., et al., Real-time non-contact cellular imaging and angiography of human cornea and limbus with common-path full-field/SD OCT. Nature Communications, 2020. 11(1): p. 1868.

Maggioni, M., et al., Nonlocal transform-domain filter for volumetric data denoising and reconstruction. IEEE transactions on image processing, 2012. 22(1): p. 119-133.

* cited by examiner

Figs. 1(a), 1(b), and 1(c)

Figs. $2(a_1)$, $2(a_2)$, $2(a_3)$, $2(b_1)$, $2(b_2)$, $2(b_3)$, $2(c_1)$, $2(c_2)$, $2(c_3)$, $2(d_1)$, $2(d_2)$, $2(d_3)$, $2(e_1)$, $2(e_2)$, $2(e_3)$, $2(f_1)$, $2(f_2)$, and $2(f_3)$ Figs. 3($a_1$), 3($a_2$), 3($a_3$), 3($b_1$), 3($b_2$), 3($b_3$), 3($c_1$), 3($c_2$), 3($c_3$), 3($d_1$), 3($d_2$), 3($d_3$), 3($e_1$), 3($e_2$), 3($e_3$), 3($f_1$), 3($f_2$), 3($f_3$), 3($g_1$), 3($g_2$), 3($g_3$), and 3(h)

Figs. 4($a_1$), 4($a_2$), 4($a_3$), 4($b_1$), 4($b_2$), 4($b_3$), 4($c_1$), 4($c_2$), 4($c_3$), 4($d_1$), 4($d_2$), 4($d_3$), 4($e_1$), 4($e_2$), 4($e_3$), 4(e4), 4(e5), and 4(e6)

Figs. 5($a_1$), 5($a_2$), 5($a_3$), 5($b_1$), 5($b_2$), 5($b_3$), 5($c_1$), 5($c_2$), 5($c_3$), 5($d_1$), 5($d_2$), 5($d_3$), 5($e_1$), 5($e_2$), 5($f_1$), 5($f_2$), 5($g_1$), and 5($g_2$)

Figs. 6($a_1$), 6($a_2$), 6($a_3$), 6($b_1$), 6($b_2$), 6($b_3$), 6($c_1$), 6($c_2$), 6($c_3$), 6($d_1$), 6($d_2$), 6($d_3$), 6($e_1$), 6($e_2$), 6($e_3$), 6($f_1$), 6($f_2$), 6($f_3$), and 6(g)

Figs. 7($a_1$), 7($a_2$), 7($a_3$), 7($b_1$), 7($b_2$), 7($b_3$), 7($c_1$), 7($c_2$), and 7($c_3$)

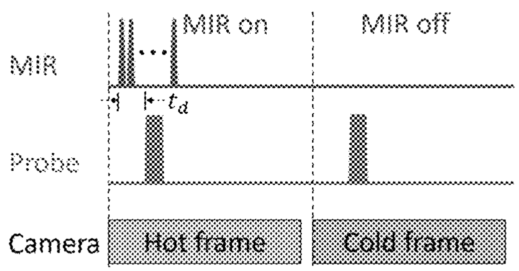
Fig. 9
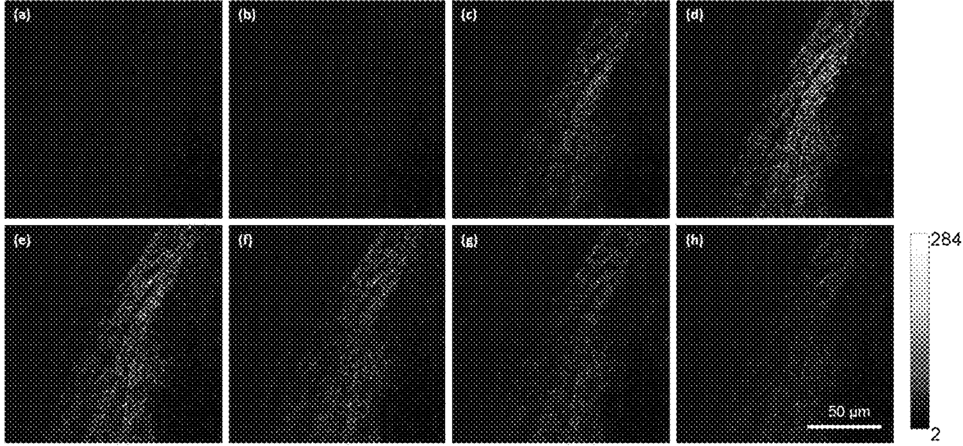
Figs. 10(a), 10(b), 10(c), 10(d), 10(e), 10(f), 10(g), and 10(h)

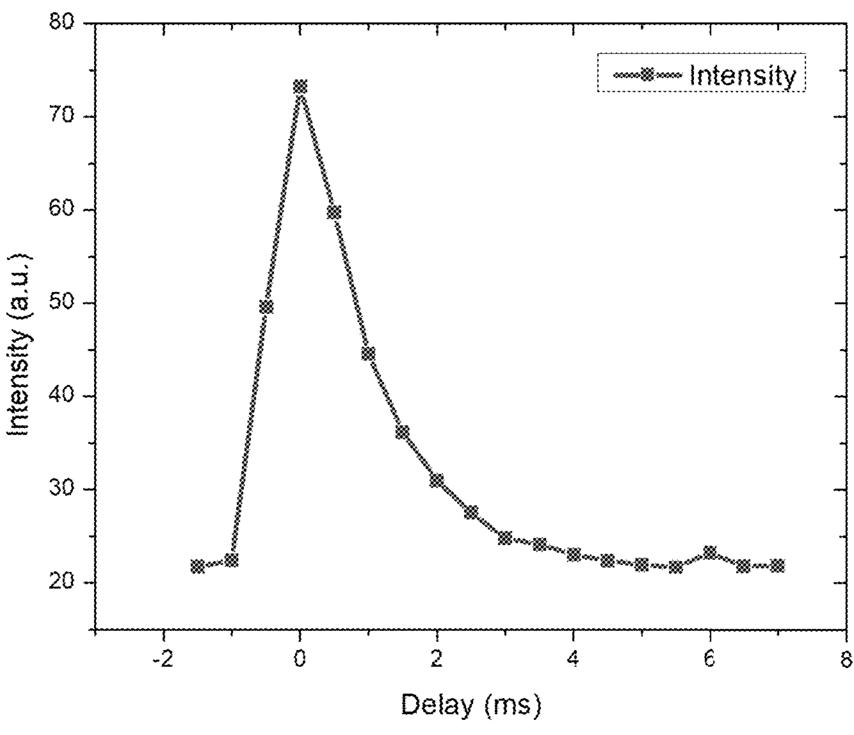
Fig. 11
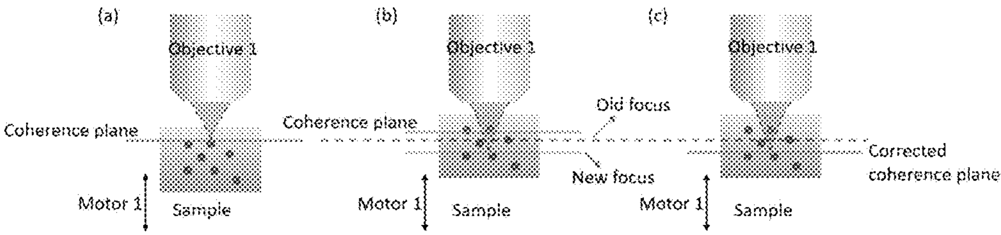
Figs. 12(a), 12(b), and 12(c)

Figs. 13(a), 13(b), 13(c), 13(d), 13(e), and 13(f)

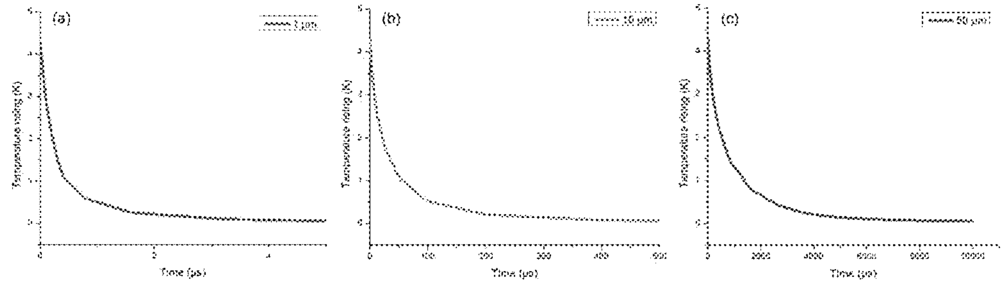
Figs. 15(a), 15(b), and 15(c)

Figs. 16($a_1$), 16($a_2$), 16($a_3$), 16($b_1$), 16($b_2$), 16($b_3$), 16($c_1$), 16($c_2$), 16($c_3$), 16($d_1$), 16($d_2$), 16($d_3$), 16($e_1$), 16($e_2$), 16($e_3$), 16($f_1$), 16($f_2$), 16($f_3$), and 16(g)

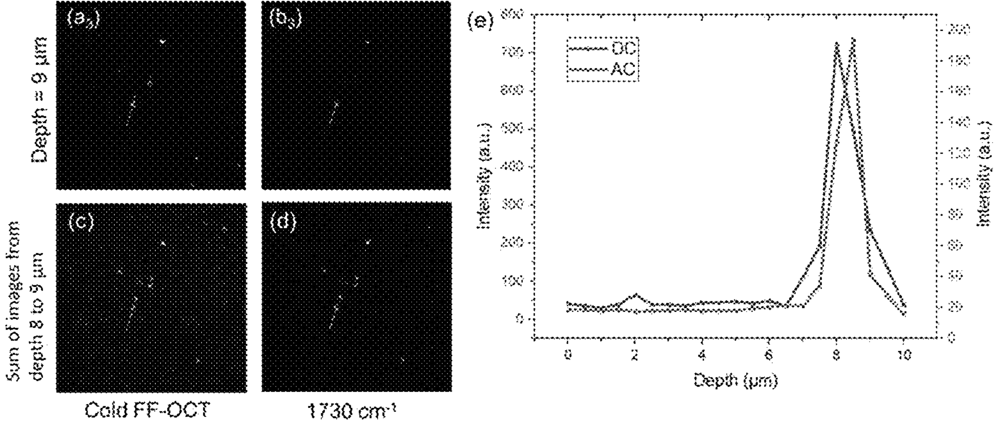
Figs. 18(a3), 18(b3), 18(c), 18(d), and 18(e)

BOND-SELECTIVE FULL-FIELD OPTICAL COHERENCE TOMOGRAPHY

CROSS REFERENCE TO RELATED APPLICATIONS

This application claims the benefit of U.S. Provisional Application No. 63/525,461, filed on Jul. 7, 2023, the entire contents of which are incorporated herein by reference.

GOVERNMENT SUPPORT

This invention was made with government support under Grant Nos. R35GM136223 and R33CA261726 awarded by the National Institutes of Health. The government has certain rights in the invention.

FIELD OF THE TECHNOLOGY

The subject disclosure relates generally to optical coherence tomography (OCT) systems and methods and, more particularly, to improvements and enhancements to OCT systems and methods.

BACKGROUND OF THE TECHNOLOGY

Optical coherence tomography (OCT) is a label-free, non-invasive three-dimensional (3D) imaging tool widely used in both biological research and clinical diagnosis. One limitation in conventional OCT modalities is that they can only visualize specimen tomography without chemical information.

SUMMARY OF THE TECHNOLOGY

According to one aspect, a wide-field bond-selective optical coherence tomography (OCT) system for imaging a sample is provided. The system includes a source of infrared light for generating infrared light, the infrared light being directed onto the sample to selectively heat the sample. A source of probe light generates probe light, the probe light being directed onto the sample. A first objective is disposed in a reference arm of the system, and a second objective is disposed in a sample arm of the system. A first actuator provides sample depth scanning with respect to the first objective, and a second actuator provides sample depth scanning with respect to the second objective. A detection system receives scattered probe light reflected from the sample.

In some exemplary embodiments, the source of probe light comprises a light-emitting diode (LED).

In some exemplary embodiments, the detection system comprises a camera. The camera can be one of a charge-coupled device (CCD) camera or a complementary metal oxide semiconductor (CMOS) camera.

In some exemplary embodiments, the infrared light is pulsed.

In some exemplary embodiments, the infrared light is mid-infrared (MIR) light.

In some exemplary embodiments, the system further comprises a movable stage for providing controllable movement for scanning the sample.

According to another aspect, a wide-field bond-selective optical coherence tomography (OCT) method for imaging a sample is provided. The method includes: generating infrared light and directing the infrared light onto the sample to selectively heat the sample; generating probe light and directing the probe light onto the sample; providing a first objective in a reference arm of the system; providing a second objective in a sample arm of the system; translating at least one of the first and second objectives to provide sample depth scanning; receiving scattered probe light reflected from the sample with a detection system; and detecting a change in received probe light that is indicative of absorption of infrared light from the sample.

In some exemplary embodiments, the probe light is generated by a light-emitting diode (LED).

In some exemplary embodiments, the scattered probe light reflected from the sample is received by a camera. The camera can be one of a charge-coupled device (CCD) camera or a complementary metal oxide semiconductor (CMOS) camera.

In some exemplary embodiments, the infrared light is pulsed.

In some exemplary embodiments, the infrared light is mid-infrared (MIR) light.

In some exemplary embodiments, the method further comprises providing controllable movement for scanning the sample.

In some exemplary embodiments, the method further comprises the step of creating a three-dimensional reconstruction of infrared absorbing regions within a sample.

In some exemplary embodiments, the camera acquires images of received scattered probe light from the sample while an intensity of infrared light to the sample is modulated.

In some exemplary embodiments, the intensity of infrared light to the sample is modulated between on and off.

In some exemplary embodiments, the method further comprises repeating the receiving and detecting steps at a plurality of relative phases between the sample and reference arms.

In some exemplary embodiments, the method further comprises repeating the receiving and detecting steps at a plurality of wavelengths of the infrared source.

In some exemplary embodiments, the method further comprises the step of producing a bond-selective 3D sectioned image of the sample.

In some exemplary embodiments, the sample is a biological tissue section. In some exemplary embodiments, the sample has a thickness of greater than 5 micrometers.

In some exemplary embodiments, the method further comprises repeating the receiving and detecting steps at a plurality of sample depths.

In some exemplary embodiments, the sample depth scanning has a range of at least 10 micrometers.

In some exemplary embodiments, the method further comprises reconstructing a 3D chemical image of the sample.

In some exemplary embodiments, the sample is highly scattering.

BRIEF DESCRIPTION OF THE DRAWINGS

FIG. 1(*b*) illustrates synchronization and image acquisition at a single depth, according to some exemplary embodiments.

FIG. 1(*c*) illustrates workflow of 3D image reconstruction, according to exemplary embodiments.

2($f_3$) illustrate BS-FF-OCT imaging of 1 μm PMMA beads embedded in agarose gel, according to some exemplary embodiments.

Figure 3:
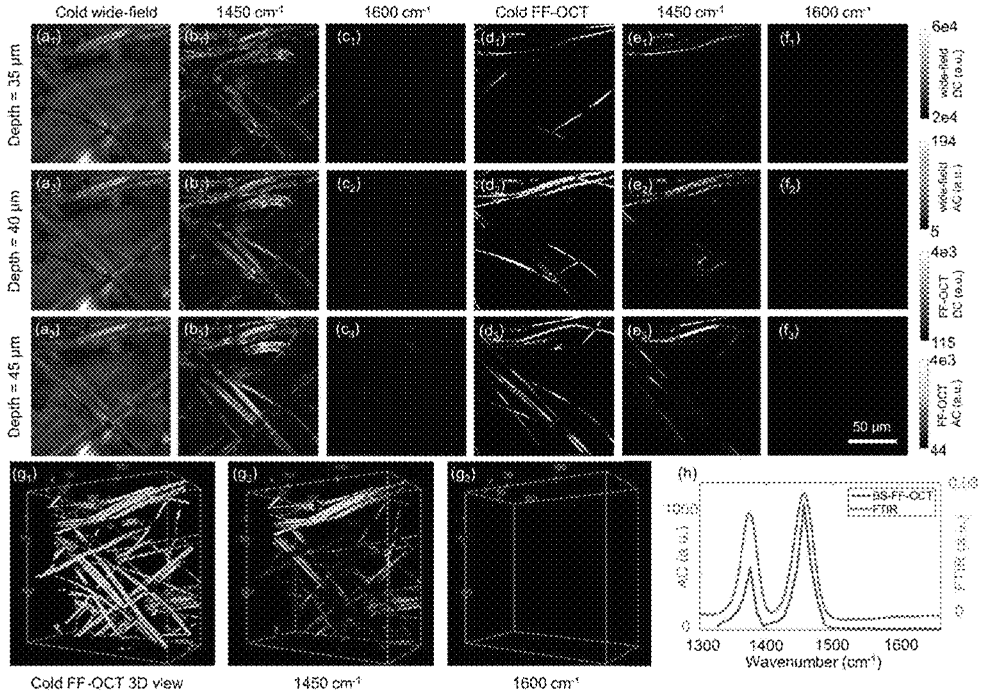

FIGS. 3($a_1$), 3($a_2$), 3($a_3$), 3($b_1$), 3($b_2$), 3($b_3$), 3($c_1$), 3($c_2$), 3($c_3$), 3($d_1$), 3($d_2$), 3($d_3$), 3($e_1$), 3($e_2$), 3($e_3$), 3($f_1$), 3($f_2$), 3($f_3$), 3($g_1$), 3($g_2$), 3($g_3$), and 3($h$) illustrate BS-FF-OCT imaging of polypropylene fiber mattress, according to some exemplary embodiments.

Figure 4:
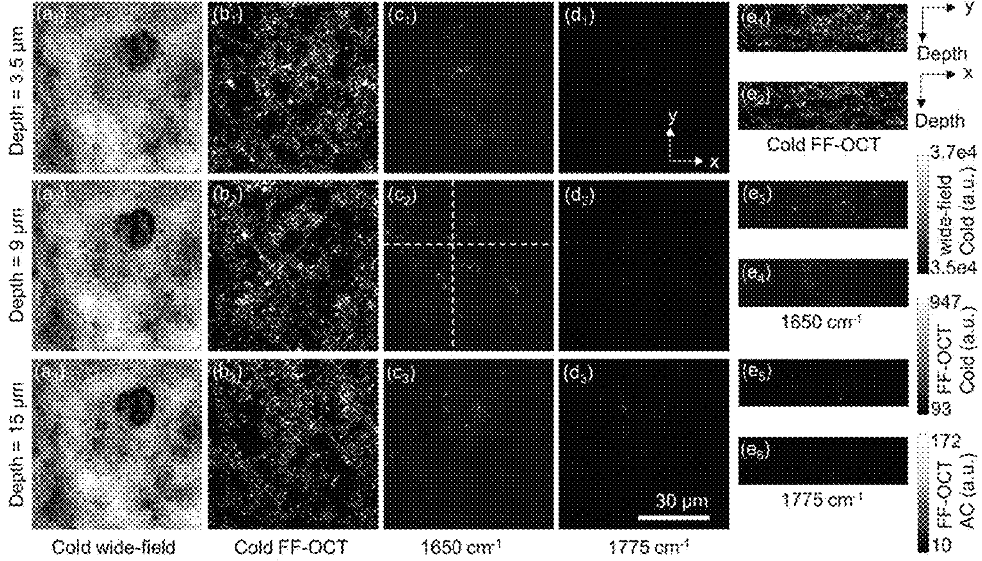

FIGS. 4($a_1$), 4($a_2$), 4($a_3$), 4($b_1$), 4($b_2$), 4($b_3$), 4($c_1$), 4($c_2$), 4($c_3$), 4($d_1$), 4($d_2$), 4($d_3$), 4($e_1$), 4($e_2$), 4($e_3$), 4($e_4$), 4($e_5$), and 4($e_6$) illustrate BS-FF-OCT imaging of cancer cell spheroids, according to some exemplary embodiments.

Figure 5:
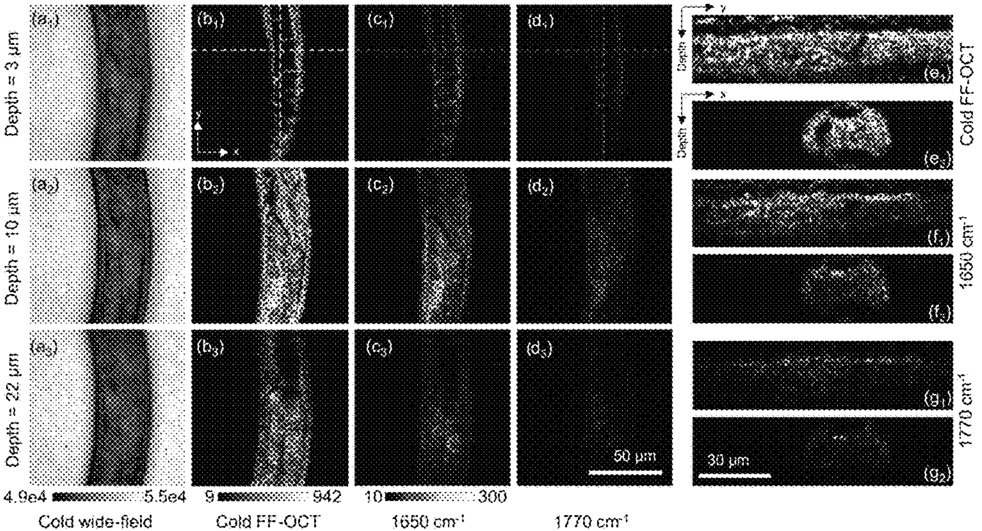

FIGS. 5($a_1$), 5($a_2$), 5($a_3$), 5($b_1$), 5($b_2$), 5($b_3$), 5($c_1$), 5($c_2$), 5($c_3$), 5($d_1$), 5($d_2$), 5($d_3$), 5($e_1$), 5($e_2$), 5($f_1$), 5($f_2$), 5($g_1$), and 5($g_2$) illustrate BS-FF-OCT imaging of *C. elegans*, according to some exemplary embodiments.

Figure 6:
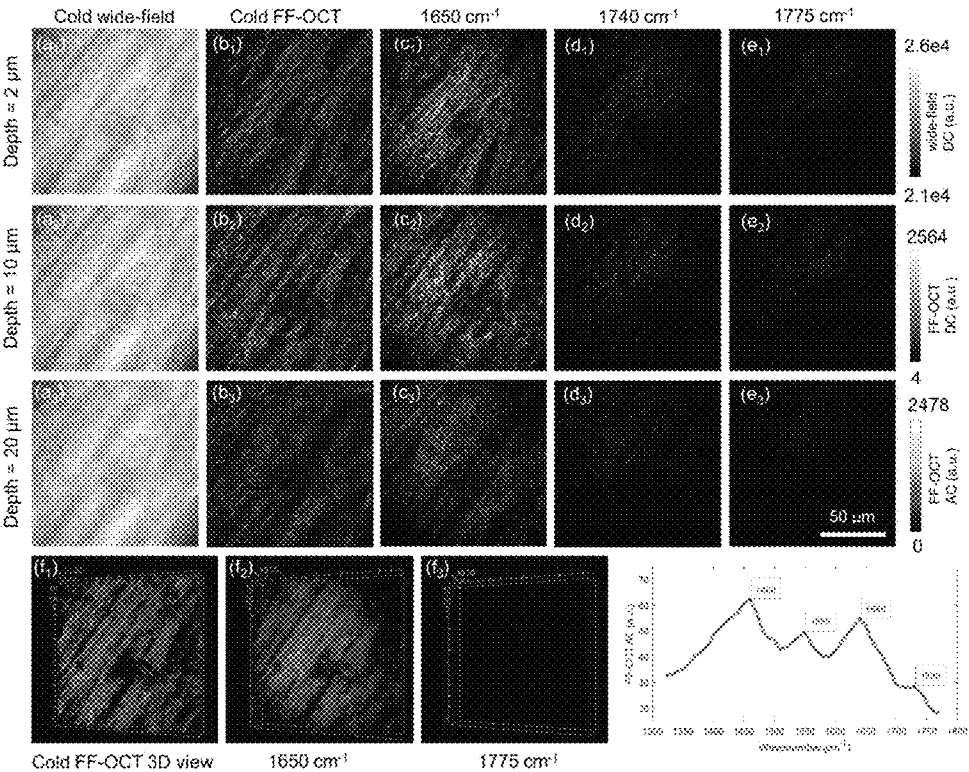

FIGS. 6($a_1$), 6($a_2$), 6($a_3$), 6($b_1$), 6($b_2$), 6($b_3$), 6($c_1$), 6($c_2$), 6($c_3$), 6($d_1$), 6($d_2$), 6($d_3$), 6($e_1$), 6($e_2$), 6($e_3$), 6($f_1$), 6($f_2$), 6($f_3$), and 6($g$) illustrate BS-FF-OCT imaging of myelinated axons in mouse brain tissue, according to some exemplary embodiments.

Figure 7:
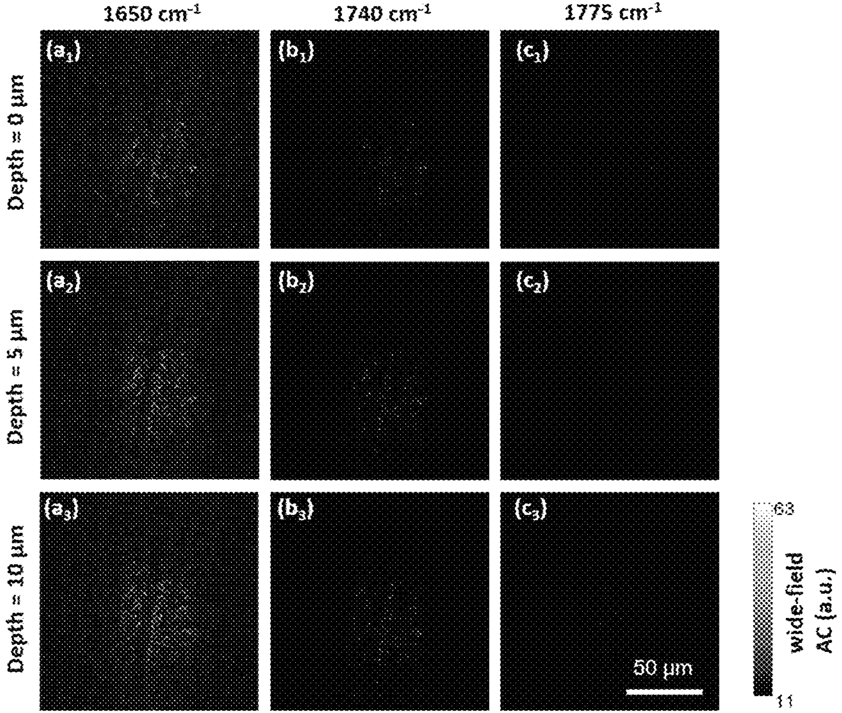

FIGS. 7($a_1$), 7($a_2$), 7($a_3$), 7($b_1$), 7($b_2$), 7($b_3$), 7($c_1$), 7($c_2$), and 7($c_3$) include widefield MIP images of myelinated axons in mouse brain tissue shown in FIGS. 6($a_1$), 6($a_2$), 6($a_3$), 6($b_1$), 6($b_2$), 6($b_3$), 6($c_1$), 6($c_2$), 6($c_3$), 6($d_1$), 6($d_2$), 6($d_3$), 6($e_1$), 6($e_2$), 6($e_3$), 6($f_1$), 6($f_2$), and 6($f_3$), according to some exemplary embodiments.

Figure 8:

FIG. 8 includes a raw BS-FF-OCT spectrum and a smoothed BS-FF-OCT spectrum of myelinated axons in mouse brain tissue in FIG. 6($g$), according to some exemplary embodiments.

FIG. 9 includes alternative timing configuration of the probe, MIR pulses, and camera of the system of the disclosure, according to some exemplary embodiments.

FIGS. 10($a$), 10($b$), 10($c$), 10($d$), 10($e$), 10($f$), 10($g$), and 10($h$) illustrate BS-FF-OCT imaging of myelinated axons in mouse brain tissue with different probe MIR pulse delay time, according to some exemplary embodiments.

FIG. 11 illustrates the BS-FF-OCT signal for different probe MIR pulse delay times, according to some exemplary embodiments.

FIGS. 12($a$), 12($b$), and 12($c$) illustrate coherence plane correction for automatic volumetric image acquisition, according to some exemplary embodiments.

FIGS. 13($a$), 13($b$), 13($c$), 13($d$), 13($e$), and 13($f$) illustrate coherence function plotting illustration, according to some exemplary embodiments.

Figure 14A:
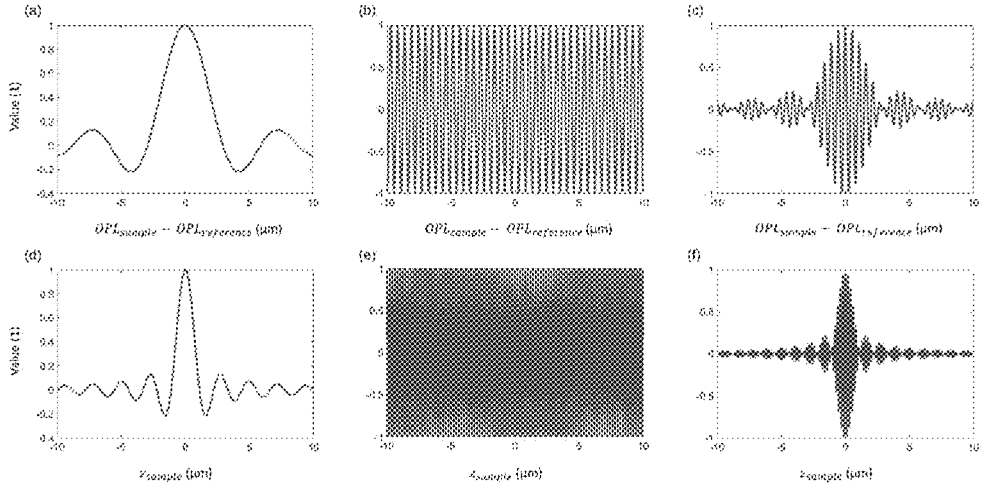
Figure 14B:
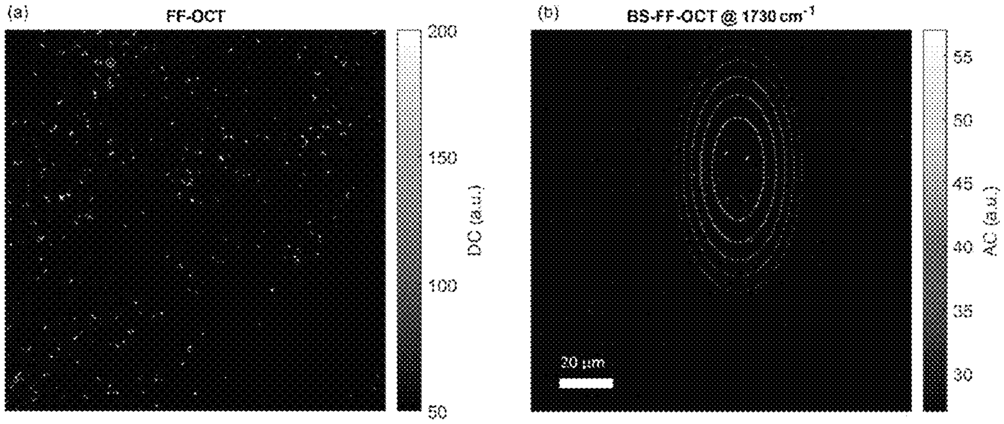

FIGS. 14($a$) and 14($b$) illustrate illumination area characterization, according to some exemplary embodiments.

FIGS. 15($a$), 15($b$), and 15($c$) illustrate a temperature cooling profile COMSOL simulation of different size PMMA beads, according to some exemplary embodiments.

FIGS. 16($a_1$), 16($a_2$), 16($a_3$), 16($b_1$), 16($b_2$), 16($b_3$), 16($c_1$), 16($c_2$), 16($c_3$), 16($d_1$), 16($d_2$), 16($d_3$), 16($e_1$), 16($e_2$), 16($e_3$), 16($f_1$), 16($f_2$), 16($f_3$), and 16($g$) illustrate BS-FF-OCT imaging of myelinated axons in mouse brain tissue, according to some exemplary embodiments.

Figure 17A:
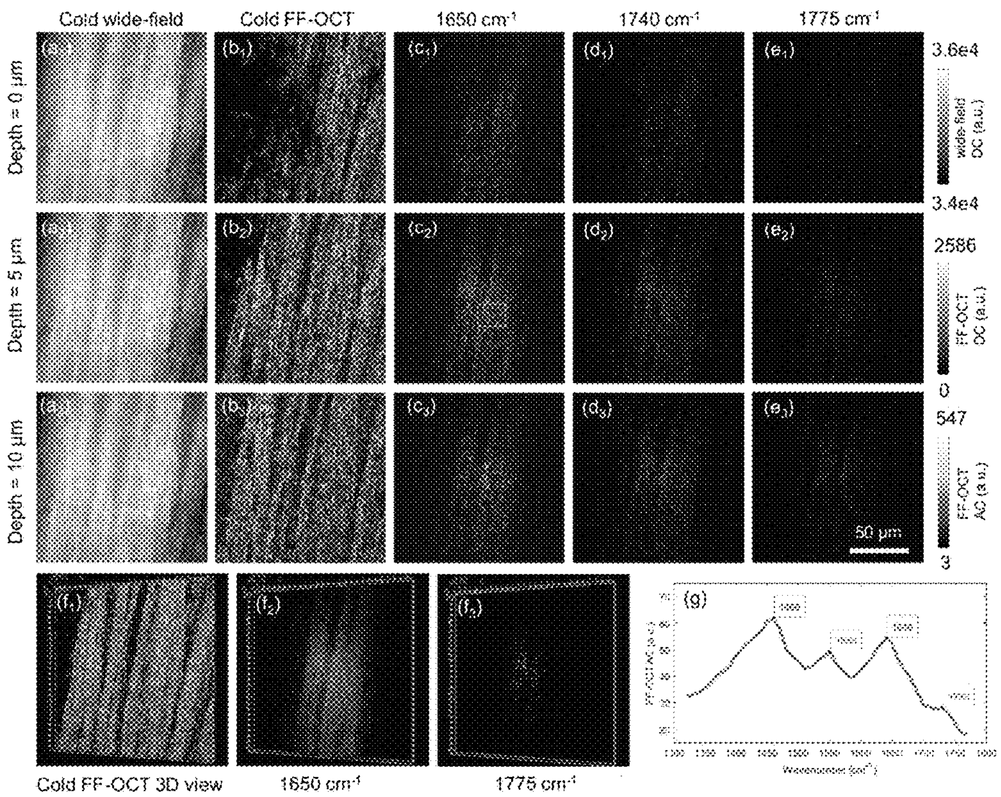
Figure 17B:
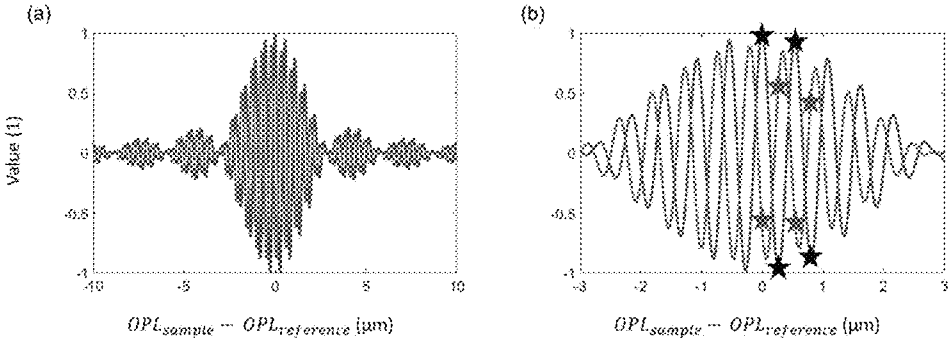

FIGS. 17($a$) and 17($b$) illustrate theoretical calculations of the coherence functions of both cold and hot states, according to some exemplary embodiments.

FIGS. 18($a_3$), 18($b_3$), 18($c$), 18($d$), and 18($e$) illustrate the BS-FF-OCT signal of PMMA beads in agargel gel, according to some exemplary embodiments.

DETAILED DESCRIPTION

According to the current disclosure, the technology described herein is directed to a bond-selective full-field OCT (BS-FF-OCT), in which a pulsed mid-infrared (MIR) laser is used to modulate the OCT signal through the photothermal effect, achieving label-free bond-selective 3D sectioned imaging of highly scattering samples. We first describe and show BS-FF-OCT imaging of 1 μm Polymethyl methacrylate (PMMA) beads embedded in agarose gel. Next, we describe and show 3D hyperspectral imaging of up to 75 μm of polypropylene fiber mattress from a standard surgical mask. We then describe and show BS-FF-OCT imaging on biological samples, including cancer cell spheroids and *C. elegans*. Using an alternative pulse timing configuration, we finally describe and show the capability of BS-FF-OCT on imaging a highly scattering myelinated axons region in a mouse brain tissue slice.

Optical coherence tomography (OCT) has experienced many advanced technical developments and demonstrated significant applications in the past decades. OCT has evolved from time-domain OCT (TD-OCT), which mechanically scans the optical phase of the reference arm to obtain the signal from different depths, to spectral-domain/Fourier-domain OCT (SD/FD-OCT), which spectrally resolves the detected interferometric signal from different depths without mechanically scanning. SD/FD-OCT has dramatically improved the sensitivity and imaging speed of OCT and achieved in vivo retinal imaging till video rate. Besides improving the scanning speed of scanning mode OCT, an alternative approach is to use multi-pixel detectors. To enable high-resolution en-face OCT imaging, time-domain full-field OCT (FF-OCT) was developed. FF-OCT adopts wide-field illumination and a multi-pixel detector (a CCD or CMOS camera) to obtain en-face images at a given depth without scanning across the sample. FF-OCT has been applied to in vivo human corneal and retinal imaging for ophthalmic diagnosis. FF-OCT has also been used for histological imaging of different types of tissues, such as human skin tissue, breast tissue, and brain tissue, for cancer diagnosis. However, those conventional FF-OCT modalities can only provide tomography images without any molecular information, which limits their potential applications to samples that have different chemical compositions but similar morphology.

Vibrational microscopy has been a widely used tool for label-free molecular imaging without sample perturbation. In these techniques, Raman scattering, or linear infrared absorption, is measured to provide contrast. More recently, the relatively weak signal and low acquisition speed of the spontaneous Raman scattering have been boosted by coherence Raman scattering microscopy. Compared to Raman scattering, which has an extremely small cross-section (~$10^{-30}$ to $10^{-28}$ $cm^2$), linear infrared (IR) absorption has ten orders of magnitude larger cross-section (~$10^{-18}$ $cm^2$). Despite the large cross-section, conventional IR imaging techniques such as Fourier transform infrared (FTIR) has poor spatial resolution due to the long illumination wavelength. To break this limitation, mid-infrared photothermal (MIP) microscopy, which indirectly measures IR absorption by using the photothermal effect, was developed recently. Since then, MIP microscopy has evolved from point-scan to wide-field configurations. As reviewed recently, MIP microscopy offers a few advantages. First, sub-micron spatial resolution is achieved through the visible probe beam. Second, wide-field MIP microscopy enables high-throughput chemical imaging by exploiting the advantage that linear IR absorption doesn't require a tight focus. By using wide-field illumination and detection configuration, the imaging speed could reach half of the camera frame rate. Third, volumetric chemical imaging is possible through mid-infrared photothermal phase tomography. Despite these advances, phase tomography, including optical diffraction tomography and intensity diffraction tomography, is limited to weakly scattering samples and can't be applied to highly scattering specimens such as tissues.

Functional OCT modalities have been developed to add additional contrast to conventional OCT. For example, polarization OCT can detect specific tissue types that can induce polarization change, spectroscopic OCT measures the spectral features within the wavelength range of the OCT light source, and thermo-elastic OCT and photothermal OCT can obtain the absorption spectrum by measuring the photothermal effect. Photothermal OCT has been a powerful functional extension of conventional OCT since it was first demonstrated in 2008. Photothermal OCT is realized by adding another modulated heating beam to the conventional OCT, and it measures the modulation of the conventional OCT signal induced by the heating beam. Firstly, it solves the inherent difficulty of OCT, or any other direct scattering-based measurement methods, distinguishing scattering and absorption. Secondly, it provides molecular specificity to OCT by only detecting signals from specific absorbers at the heating wavelength, which can be endogenous pigments originally existing in the sample, exogenous contrast agents that are imported into the sample, or overtone absorption of non-pigment endogenous chemical components. Yet, these current photothermal OCT configurations are mainly using a heating wavelength in the visible and near-infrared range, where the intrinsic absorption of biological samples is rare, which limits its wider applications. The absorption in the mid-infrared (MIR) range is more common and can provide more molecular information, which hasn't been adopted in photothermal OCT. Although there are conventional OCT modalities using MIR light sources to improve penetration depth, or a time-gated method to detect the reflection of MIR light from different depths, compared to the potential of MIR photothermal OCT, these techniques have the intrinsic MIR resolution limitation and no specificity to the absorbing molecules.

According to the current disclosure, described and shown in detail is bond-selective full-field optical coherence tomography (BS-FF-OCT), in which a pulsed MIR laser modulates the full-field OCT signal through the photothermal effect. The current technology enables label-free bond-selective 3D sectioning imaging of highly scattering thick samples. To achieve this, a modulated MIR heating beam is integrated into a time-domain FF-OCT. A broadband light-emitting-diode (LED) is used as the probe light source, and a virtual lock-in camera is used as the detector. The disclosed technology can measure the change in the OCT signal as a result of thermal expansion and refractive index change induced by MIR heating. First, we describe and show 3D bond-selective imaging of 1 μm PMMA beads embedded in agarose gel, which confirms the isotropic 1-micron resolution of BS-FF-OCT. Second, we describe and show 3D hyperspectral imaging of a polypropylene fiber mattress from a standard surgical mask and the comparison between BS-FF-OCT and FTIR to confirm the spectrum fidelity. Then, we describe and show bond-selective volumetric imaging on biological samples, including cancer cell spheroids and *C. elegans*. Finally, we describe and show the capability of the BS-FF-OCT setup on imaging a highly scattering biological sample, i.e., myelinated axons in a mouse brain tissue slice, using an alternative pulse timing configuration.

Figure 1:
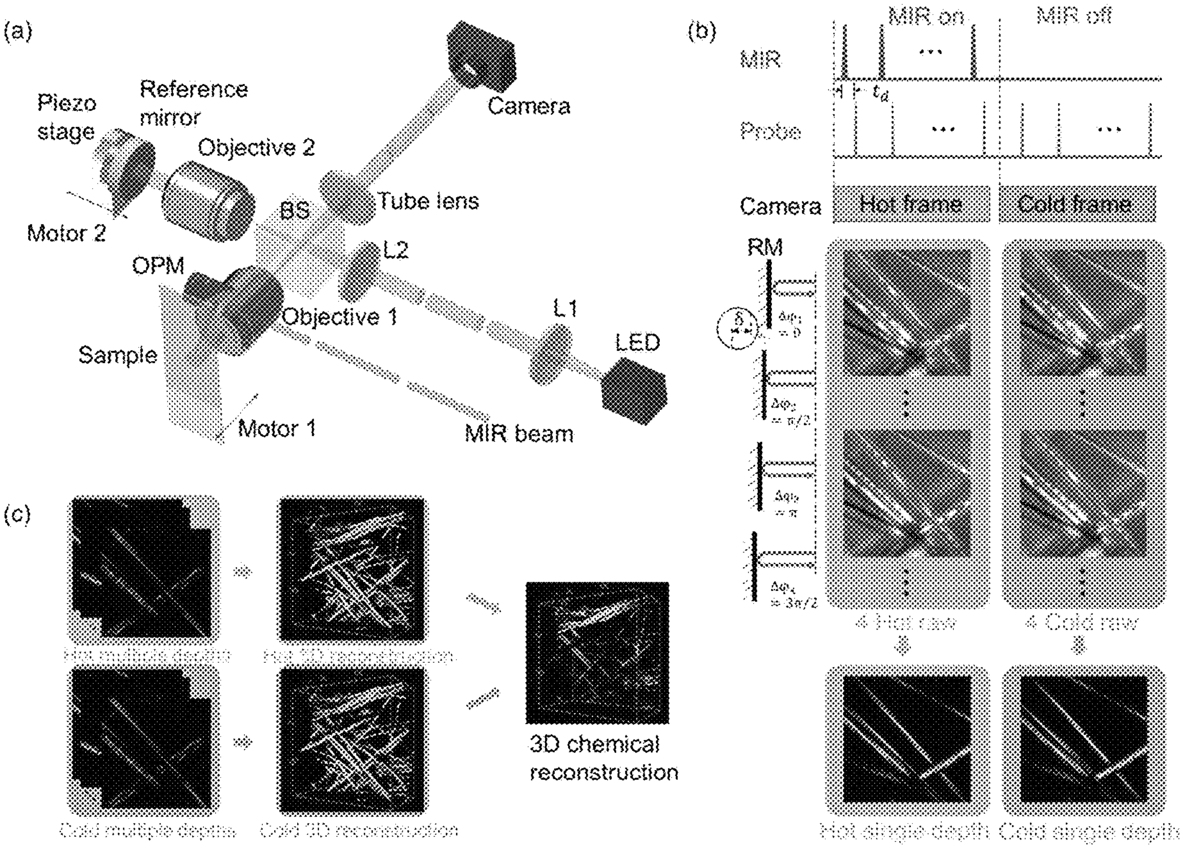
FIG. 1(*a*) includes a schematic diagram of the bond-selective full-field OCT (BS-FF-OCT) system setup, according to some exemplary embodiments.

FIG. 1(*a*) includes a schematic diagram of the bond-selective full-field OCT (BS-FF-OCT) system setup, according to some exemplary embodiments. Referring to FIGS. 1(*a*), 1(*b*), and 1(*c*), the full-field optical coherence tomography (FF-OCT) is based on a Michelson interferometer. A broadband light-emitting diode LED (for example, UHP-T-545-SR, Prizmatix) provides Köhler illumination in both a sample arm and a reference arm of the system. Air objectives (for example, SLMPLN50X, Olympus) are used in both the sample and reference arms. That is, objective 1 is disposed in the sample arm of the system, and objective 2 is disposed in the reference arm of the system. A CMOS camera (for example, BFS-U3-17S7, FLIR) captures the wide-field interferometric image. The MIR beam is emitted by a mid-infrared optical parametric oscillator (for example, Firefly-LW, M Squared Lasers), tunable from 1320 $cm^{-1}$ to 1775 $cm^{-1}$. In some exemplary embodiments, the laser outputs a 20 kHz MIR pulse train. Then, the 20 kHz MIR pulse train is modulated at, for example, 50 Hz by an optical chopper system (for example, MC2000B, Thorlabs). The modulated MIR beam is focused by an off-axis parabolic mirror (OPM) (for example, MPD019-M03, Thorlabs) at the same side of the sample that the LED illuminates. The MIR pulse, LED probe pulse, optical chopper, and camera are synchronized by a pulse generator (for example, 9254-TZ50-US, Quantum composers) similar to the type used in wide-field MIP microscopy. The synchronized camera can capture exactly the corresponding images when the MIR beam is modulated on and off (corresponding "hot" and "cold" states of the sample). The details of the MIR and probe beam parameter, including the pulse widths, delays, powers, and illumination area are described below in connection with FIGS. 14(*a*) and 14(*b*) and Table 1. The reference mirror is installed on a piezo stage (for example, MIPOS 100 SG RMS, Piezosystem Jena) to shift the phase difference between the two arms, i.e., the sample arm and the reference arm. Both reference mirror (with the piezo stage) and sample are installed on actuators (e.g. motorized stages, for example, Z825B, Thorlabs) to achieve automated and synchronized coherence and focal plane matching for volumetric image acquisition. Other suitable actuators can include piezoelectric, voice coil, electrostrictive, magnetostrictive, microelectromechanical systems (MEMS), ultrasonic, thermoelectric, electrohydraulic, stepper motors, linear motors, flexure-based, electrostatic, or any other actuator that produces translation in response to a control signal.

The coherence plane shifting in FF-OCT is critical to match objective focal and coherence planes. The coherence plane shift and its correction are illustrated herein in FIGS. 12(*a*), 12(*b*), and 12(*c*). When the system is imaging a specific depth of a sample, the coherence plane has to overlay with the focal plane (FIG. 12(*a*)). Then motor 1 scans the sample to the next depth. The coherence plane shifts and does not overlay with the new focal plane (FIG. 12(*b*)). Then, motor 2 must scan a certain distance of the reference mirror to make the coherence plane overlay with the new focal plane (FIG. 12(*c*)). Software is developed to achieve automatic volumetric data acquisition in BS-FF-OCT. The software can automatically correct the coherence plane position by linearly shifting the reference mirror position at each depth during the multi-depth scanning, i.e., shifting $\Delta z/n$ at each depth in an $(n+1)$-depths multi-depth acquisition, where $\Delta z$ is the reference mirror shifting distance between the initial depth and the final depth. Manual correction is needed only at the initial depth and the final depth. The coherence plane can be corrected by linearly shifting the reference mirror position because the correction distance of the coherence plane has a linear relation with the sample shifting distance, as shown in the following equation, $$\Delta z_{coherence\ plane} = \Delta z_{sample} \cdot \frac{n_{sample}^2 - n_{immersion}^2}{n_{sample} \cdot n_{immersion}} \quad (1)$$

where the $n_{sample}$ is the refractive index of the sample, and $n_{immersion}$ is the refractive index of the immersion medium. $n_{immersion}$ is a constant and $n_{sample}$ can be treated approximately as a constant for a common sample that usually does not contain large refractive index changes within the data acquisition depth range.

The theory of the image reconstruction process at a specific depth of the sample is summarized below. With continued reference to FIGS. 1(*a*) through 1(*c*), at a specific depth (i.e., depth i) of the sample, 4 "cold" and 4 "hot" images are captured by the camera with four different phase shift values between the sample arm and the reference arm. The detected photothermal FF-OCT image from the sample's depth i, $$I_{photothermal}^{i},$$

is reconstructed using the equation below (detailed derivation is shown below in additional detailed description)

$$I_{photothermal}^{i} = \sqrt{\left(I_1^{cold} - I_3^{cold}\right)^2 + \left(I_2^{cold} - I_4^{cold}\right)^2} - \sqrt{\left(I_1^{hot} - I_3^{hot}\right)^2 + \left(I_2^{hot} - I_4^{hot}\right)^2} \quad (2)$$

The photothermal image at the sample's depth i reconstructed by equation (2) can be further expressed as follows, $$I_{photothermal}^{i} = \Delta E_{sample} + E_{sample}^{cold} \cdot [1 - \Gamma(\Delta OPL_{sample})] \quad (3)$$

where $$E_{sample}^{cold},$$

is the reflection field from the sample's depth i in the "cold" state of the sample. The $\Delta E_{sample}$ and $\Gamma(\Delta OPL_{sample})$ represent the photothermal-induced reflection field change and coherence change, respectively. The detailed definitions are shown below in the additional detailed description material.

Then a 1-D model of the sample is analyzed to further explain the origin of the detected photothermal signal by calculating $\Delta E_{sample}$, $$E_{sample}^{cold}$$

and $\Delta OPL_{sample}$ in equation (3). It is assumed there is a target layer at the depth i (the depth is $z_i$) of the sample, and the refractive index (for the probe wavelength) of the target layer is $n_{target}$. It is additionally assumes that the part above this target layer is a uniform medium with a refractive index (for the probe wavelength) of $n_{medium}$ (assuming $n_{target} > n_{medium}$). It is additionally assumed that the MIR absorption coefficient of the target layer is much larger than the medium (which is true since the medium is usually carefully chosen to avoid MIR absorption), thus the temperature change of the target layer, $\Delta T_{target}$, is much larger than the medium, $\Delta T_{medium}$. Assuming the medium attenuation coefficients of the MIR beam and the probe beam are $\mu_{MIR\ att\ medium}$ and $\mu_{probe\ att\ medium}$, then the MIR intensity and the probe intensity at depth i can be written as, $I_{MIR}(z_i) = I_{MIR}(0) \cdot e^{-\mu_{MIR\ att\ medium} \cdot z_i}$, $I_{probe}(z_i) = I_{probe}(0) \cdot e^{-\mu_{probe\ att\ medium} \cdot z_i}$, respectively. Then the probe field at depth i can be written as $$E_{probe}(z_i) = E_{probe}(0) \cdot e^{-\frac{1}{2}\mu_{probe\ att\ medium} \cdot z_i}.$$

Then the reflection field at depth i, $$E_{sample}^{cold}$$

can be written as, (considering the attenuation of the returning trip, the ½ factor disappears)

$$E_{sample}^{cold} = E_{probe}(0) \cdot e^{-\mu_{probe\ att\ medium} \cdot z_i} \cdot \frac{n_{target} - n_{medium}}{n_{target} + n_{medium}} \quad (4)$$

The optical path length can be written as, $$OPL_{sample}^{cold} = 2 \cdot z_i \cdot n_{medium} \quad (5)$$

Differentiating equations (4) and (5) with temperature T, and considering $$\Delta T_{target} \propto I_{MIR}(z_i),\ \Delta T_{medium} \propto \int_0^{z_i} I_{MIR}(z)dz/z_i$$

(average MIR intensity over the depth range of the medium), $\Delta E_{sample}$ and $\Delta OPL_{sample}$ can be approximated as, $$\Delta E_{sample} \approx E_{probe}(0) \cdot e^{-\frac{1}{2}\mu_{probe\ att\ medium} \cdot z_i} \cdot \frac{1}{(n_{target} + n_{medium})^2} \cdot \frac{\partial n_{target}}{\partial T} \cdot \Delta T_{target} \propto e^{-\frac{1}{2}\mu_{probe\ att\ medium} \cdot z_i} \cdot e^{-\mu_{MIR\ att\ medium} \cdot z_i} \quad (6)$$

$$\Delta OPL_{sample} \approx \left(\frac{\partial n_{medium}}{\partial T} + \frac{\partial l_{medium}}{l \cdot \partial T} \cdot n_{medium}\right) \cdot 2 \cdot z_i \cdot \Delta T_{medium} \propto (1 - e^{-\mu_{MIR\ att\ medium} \cdot z_i}) \quad (7)$$

In which the $$\frac{\partial n_{target}}{\partial T},\ \frac{\partial n_{medium}}{\partial T},\ \text{and}\ \frac{\partial l_{medium}}{l \cdot \partial T}$$

are the thermo-optic and thermal-expansion coefficients of the target or the medium, respectively.

Equation (3) shows that the detected photothermal FF-OCT signal includes both the signal from $\Delta E_{sample}$ (change of the reflection of one specific target layer) and $\Delta OPL_{sample}$ (change of the optical path length of all the layers above the target layer). The interferograms of the coherence functions of the hot and cold states in FIG. 17 can also intuitively show that the measured photothermal signal is from both parts. Although the photothermal-induced change from the $\Delta E_{sample}$ is usually small (compared with $$E_{sample}^{cold})$$

due to the small thermo-optic coefficient (~$10^{-4}$), the signal from the $$E_{sample}^{cold} \cdot [1 - \Gamma(\Delta OPL_{sample})]$$

can be much larger due to the $\Delta OPL_{sample}$ increasing with depth and can be comparable to $$E_{sample}^{cold}$$

(when $\Delta OPL_{sample}$ is comparable to the coherence length). From equations (6) and (7), we can see that $\Delta E_{sample}$ decreases when the detection depth increases due to the attenuation of both the MIR and the probe beam, which usually induces a "shadow effect" for the deeper layers. $\Delta OPL_{sample}$ increases when the detection depth increases due to the accumulated depth range being heated by the MIR beam increase, which can decrease the "shadow effect".

The sensitivity of the FF-OCT setup is defined by the minimum detectable (when SNR=1) coherent reflection of the sample ($R_{min}$), $$R_{min} = 0.4 \cdot \frac{(R_{ref} + 2R_{inc})^2}{N \xi_{sat} R_{ref}} \tag{8}$$

in which, the $R_{ref}$ is the reflection of the reference mirror (4% in some exemplary embodiments), $R_{inc}$ is the incoherent reflection from the sample, which is about 10% in some exemplary embodiments, N is the number of total images acquired (average 100 images in some exemplary embodiments), $\xi_{sat}$ is the full well capacity of the camera (100 k in some exemplary embodiments).

Substituting all of those values, $R_{min}$ for some exemplary embodiments is about $5.8\times10^{-8}$. The actually measured coherent reflection of the samples, cell spheroids: 0.06%, *C. elegans:* 0.1%, and brain tissue: 0.4%, are all far beyond the theoretical sensitivity limit of the exemplary FF-OCT system.

Regarding sample preparation, polymethyl methacrylate (PMMA) beads embedded in agar gel sample preparation process is as follows. 1 mg agarose powder (Ultrapure Agarose, 16500-500) is measured and blended with 800 μL DI water and 200 μL 1 μm PMMA bead suspension (Phosphorex, MMA1000). Then the suspension is heated on a 95° C. hot plate until the agarose powder is melted. One 50 μm thick spacer is put on top of a $CaF_2$ substrate. Then the $CaF_2$ substrate with the space and a $CaF_2$ coverslip are preheated to 95° C. to avoid instant solidification when the hot agar gel suspension contacts with the cold $CaF_2$ substrate or coverslip. The temperature of the sample suspension and the $CaF_2$ substrate is below 100° C. to avoid water boiling during sample preparation. 50 μL hot sample suspension is dropped on the $CaF_2$ substrate, and then the $CaF_2$ coverslip is put on top of the $CaF_2$ substrate to sandwich the sample suspension. Finally, the sample cools down at room temperature and solidifies.

The polypropylene fiber mattress sample is made by peeling off the melt-blown fabric layer from a regular surgical mask. Then the polypropylene fiber layer is fixed on a silicon substrate by double-sided tape.

The mouse brain tissue, *C. elegans*, and T24 human bladder cancer cell spheroids sample are prepared as follows. First, the fresh mouse brain (Charles River Labs Inc, BIOSPECIMEN-BRAIN-MOUSE) is fixed in 10% formalin and sliced into 150-μm-thick slices. The wild type *C. elegans* adults and T24 human bladder cancer cell spheroids are fixed in 10% formalin. Then the samples are washed in $D_2O$-based phosphate-buffered saline (PBS) buffer three times. Then, the washed samples are sandwiched between the $CaF_2$ substrate and the $CaF_2$ coverslip. Finally, the gap between the substrate and the coverslip is sealed with nail polish.

Regarding images denoising, the BM4D denoising method is by an open-source demo software for BM4D volumetric data denoising (release ver. 3.2, 30 Mar. 2015). The parameter values used are as follows. Noise standard deviation given as the percentage of the maximum intensity of the signal, 11%; noise distribution is Gaussian; BM4D parameter profile, modified profile; enable Wiener filtering; verbose mode; enable sigma estimation.

Regarding FTIR measurement, the FTIR spectrum is measured by a commercial FTIR spectroscopy (for example, Nicolet FT-IR with ATR), which is a high-end optical benchtop system with 0.09 $cm^{-1}$ resolution and continuous dynamic alignment. This unit allows AutoTune and automated continuously variable aperture adjustment. A horizontal attenuated total reflectance (HATR) accessory is also available.

Regarding spectrum smoothing, the Gaussian-weighted moving average filter used in this work is realized by the "smoothdata" function in MATLAB R2021b. "Gaussian" window is chosen.

Referring again to FIGS. 1(*a*), 1(*b*), and 1(*c*), the BS-FF-OCT system of the current technology includes a beam splitter BS, two lenses L1 and L2, light-emitting diode LED, reference mirror RF, camera, and off-axis parabolic mirror (90 degrees) OPM.-FF-OCT setup, synchronization, and image processing. (a) BS-FF-OCT setup configuration. BS: Beam-splitter. L1-2: Lens. LED: Light-emitting-diode. OPM: Off-axis parabolic mirror (90 degrees). FIG. 1(*b*) illustrates synchronization and image acquisition at a single depth, according to some exemplary embodiments. Camera captures "hot" and "cold" frames, where the MIR beam is respectively on and off in a sequence. MIR and probe pulses are synchronized, and the time delay ($t_d$) between them is optimized to detect the maximum photothermal signal. The reference mirror is shifted a certain distance (δ) 4 times to create 4 pairs (hot and cold) interference raw images, and then a pair of FF-OCT images at a specific depth is obtained by image processing. FIG. 1(*c*) illustrates workflow of 3D image reconstruction, according to exemplary embodiments. By combining FF-OCT images at multiple depths, 3D reconstruction images can be obtained. Finally, 3D bond-selective image can be obtained by subtracting the hot and cold 3D images. The sample in the demonstration figures is a polypropylene fiber mattress, which will be described in more detail below in connection with FIGS. FIGS. 3($a_1$), 3($a_2$), 3($a_3$), 3($b_1$), 3($b_2$), 3($b_3$), 3(1), 3($c_2$), 3($c_3$), 3($d_1$), 3($d_2$), 3($d_3$), 3($e_1$), 3($e_2$), 3($e_3$), 3($f_1$), 3($f_2$), 3($f_3$), 3($g_1$), 3($g_2$), 3($g_3$), and 3(*h*).

Continuing to refer to FIGS. 1(*a*), 1(*b*), and 1(*c*), BS-FF-OCT according to the current disclosure uses the modulation of the OCT signal by the photothermal effect induced by the MIR beam. The setup shown in FIG. 1(*a*) is compartmentalized into two sub-systems: (1) FF-OCT and (2) MIR modulation. For the FF-OCT part, the light source is a broadband light-emitting-diode LED (central wavelength: 545 nm, FWHM: 100 nm). The reference mirror (reflectivity: 4%) is placed on a piezo scanner to create phase shifting between the reference and sample arms. Both the sample and reference mirrors are installed on motorized stages to scan different depths of the sample. For the MIR modulation part, a tunable MIR laser from 1320 $cm^{-1}$ to 1775 $cm^{-1}$ (linewidth: 10 $cm^{-1}$), covering the fingerprint region is used. The MIR and probe beams illuminate the sample from the same side.

The setup captures the depth-resolved photothermal FF-OCT images at a specific depth of the sample using a virtual lock-in technique, as shown in FIG. 1(*b*). The top panel of FIG. 1(*b*) shows the timing configuration of the probe, MIR pulses, and camera exposure. The MIR pulse has a 20 kHz repetition rate and is modulated to "on" and "off" duty cycles by an optical chopper at 50 Hz. The probe pulse repetition rate is also set to 20 kHz which is synchronized with the MIR pulse with a specific delay time to optimize the photothermal signal. The optimized delay time usually equals zero when the photothermal signal is majorly from the absorber itself rather than the surrounding medium. The camera frame rate is 100 Hz and is synchronized with the modulated "on" and "off" duty cycles of the MIR pulse. The camera-captured frames that correspond to the "on" and "off" duty cycles are called "hot" and "cold" frames, respectively. The middle panel of FIG. 1(*b*) shows that at each phase position of the reference mirror, a set of "hot" and "cold" raw frames are captured (to be averaged to 1 "hot" frame and 1 "cold" frame), and there are in total 4 phase positions. The bottom panel of FIG. 1(*b*) shows that 1 "hot" or "cold" FF-OCT image is obtained from the 4 "hot" or "cold" averaged raw frames, using the 4-frame phase-shifting algorithm (as the detailed derivations set forth below in the additional descriptive material). Then, the depth-resolved photothermal FF-OCT image at this specific depth can be obtained by subtracting the "hot" and "cold" FF-OCT images as shown in the equations herein. Furthermore, to obtain 3D reconstructed images for both hot and cold states, as shown in FIG. 1(*c*), the sample is scanned at different depths with automatic coherence plane correction within the imaging volume as described herein in detail. A 3D bond-selective OCT map can be obtained by subtracting the hot and cold 3D reconstructed images.

Figure 2:
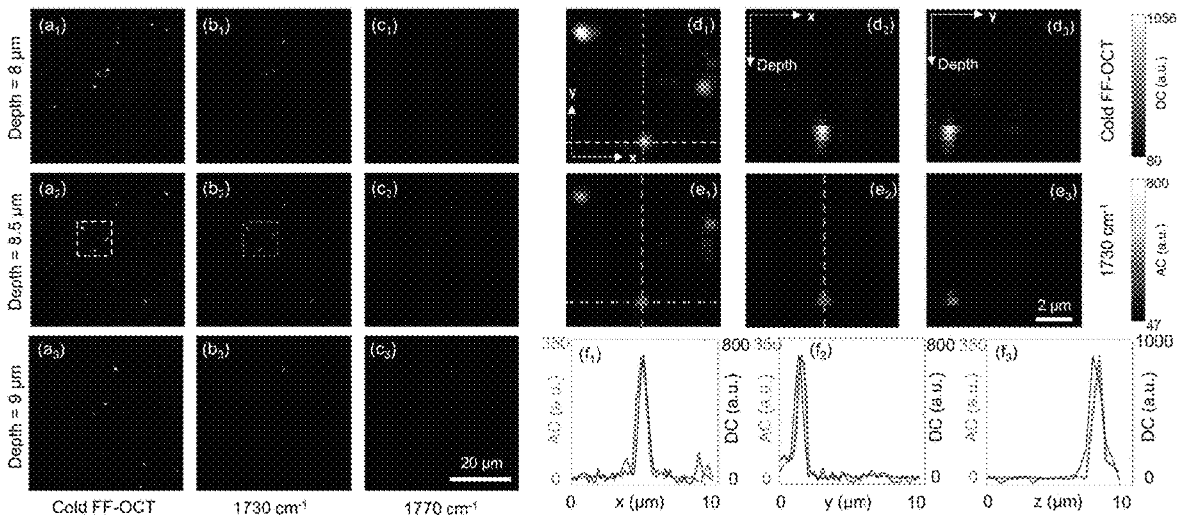
FIGS. 2($a_1$), 2($a_2$), 2($a_3$), 2($b_1$), 2($b_2$), 2($b_3$), 2($c_1$), 2($c_2$), 2($c_3$), 2($d_1$), 2($d_2$), 2($d_3$), 2($e_1$), 2($e_2$), 2($e_3$), 2($f_1$), 2($f_2$)

FIGS. 2($a_1$), 2($a_2$), 2($a_3$), 2($b_1$), 2($b_2$), 2($b_3$), 2($c_1$), 2($c_2$), 2($c_3$), 2($d_1$), 2($d_2$), 2($d_3$), 2($e_1$), 2($e_2$), 2($e_3$), 2($f_1$), 2($f_2$), and 2($f_3$) illustrate BS-FF-OCT imaging of 1 μm PMMA beads embedded in agarose gel, according to some exemplary embodiments. Specifically, FIGS. 2($a_{1-3}$) illustrated cold FF-OCT images at different depths. FIGS. 2($b_{1-3}$) and 2 ($c_{1-3}$) illustrate BS-FF-OCT images at 1730 cm-1 and 1770 cm-1. 1730 cm-1 is the C—O band in PMMA, and 1770 cm-1 is at off-resonance. FIG. 2($d_1$) illustrates zoom-in view of the white dashed square area in FIG. 2($a_2$). FIG. ($d_{2-3}$) are cross-sectional images along the dashed lines in FIG. ($d_1$). FIGS. ($e_{1-3}$) include corresponding BS-FF-OCT images at 1730 cm-1 of FIGS. ($d_{1-3}$). FIGS. ($f_{1-3}$) include 1D cross-line profiles corresponding to the dashed lines in FIGS. ($e_{1-2}$). The black profiles correspond to the cold FF-OCT images. FWHM of line profiles: 942.5 nm (green in ($f_1$)), 824.4 nm (black in ($f_1$)), 787.3 nm (blue in ($f_2$)), 772.7 nm (black in ($f_2$)), 870.3 nm (purple in ($f_3$)) and 1156.7 nm (black in ($f_3$)). BS-FF-OCT images are normalized by MIR powers. All intensity values are in linear scales. Image sizes: FIGS. 2(*a-c*) 50 μm (280 pixels)×50 μm (280 pixels), FIGS. ($d_1$, $e_1$) 10 μm (56 pixels)×10 μm (56 pixels), FIGS. ($d_{2-3}$, $e_{2-3}$) 10 μm (56 pixels)×10 μm (20 depths).

To characterize the BS-FF-OCT system setup, 3D bond-selective imaging of 1 μm Poly(methyl methacrylate) (PMMA) beads embedded in agarose gel is described. FIGS. 2($a_1$), 2($a_2$), 2($a_3$), 2($b_1$), 2($b_2$), 2($b_3$), 2($c_1$), 2($c_2$), 2($c_3$), 2($d_1$), 2($d_2$), 2($d_3$), 2($e_1$), 2($e_2$), 2($e_3$), 2($f_1$), 2($f_2$), and 2($f_3$) show that BS-FF-OCT of the present disclosure achieves label-free volumetric vibrational spectroscopic imaging at isotropic 1-micron resolution. Specifically, FIGS. 2(*a-c*) show the cold FF-OCT, on-resonance, and off-resonance BS-FF-OCT images captured at three different depths with 0.5 μm step size. First, the cold FF-OCT images in FIG. 2(*a*) distinguish beads suspended at different depths (i.e., 1 μm apart), showing the depth-resolving capability of BS-FF-OCT setup. Second, to demonstrate the bond-selective capability, the MIR beam is set to an on-resonance absorption peak of PMMA at 1730 $cm^{-1}$. The BS-FF-OCT images show consistent features as in cold FF-OCT images (see FIGS. 2(*a-b*). Yet, the off-resonance BS-FF-OCT images at 1770 $cm^{-1}$ show weak contrast of beads, as shown in FIG. 2(*c*). FIGS. 2(*d-e*) are the zoom-in views of a selected imaging 3D volume from three different directions. FIGS. 2($d_1$) and FIG. 2($e_1$) are the corresponding areas indicated by the dashed squares in FIG. 2($a_2$) and FIG. 2($b_2$), respectively. It can be seen from FIGS. 2(*d-e*) that the beads have a slightly longer dimension along the optical axis. To characterize the axial and lateral resolution quantitatively, the 1D line profiles across the selected bead are plotted in FIG. 2(*f*). The full-width half maximum (FWHM) of these line profiles are as follows, 942.5 nm (green in ($f_1$)), 824.4 nm (black in ($f_1$)), 787.3 nm (blue in ($f_2$)), 772.7 nm (black in ($f_2$)), 870.3 nm (purple in ($f_3$)) and 1156.7 nm (black in ($f_3$)). This result demonstrates the isotropic 1-μm resolution of the BS-FF-OCT setup. As a pump-probe technique, the resolution of the BS-FF-OCT setup is determined by the wavelength and optics of the probe beam. For FF-OCT, the axial resolution (Δz) can be calculated as $$\Delta z = \left(\frac{1}{\Delta z_s^2} + \frac{1}{\Delta z_{NA}^2}\right)^{-\frac{1}{2}}, \text{ where } \Delta z_s = \frac{2\ln(2)}{n\cdot\pi}\cdot\frac{\lambda_0^2}{\Delta\lambda},$$

which corresponding the coherence length, and $$\Delta z_{NA} = \frac{n\cdot\lambda_0}{NA^2},$$

which corresponding to the focal depth. The lateral resolution (Δr) can be calculated as $$\Delta r = \frac{\lambda_0}{2\cdot NA}.$$

Substituting $\lambda_0$=545 nm, $\Delta\lambda$=100 nm, n=1.33, NA=0.35, the theoretical axial resolution $\Delta z$ can be calculated to be 972.1 nm, $\Delta z_s$=985.5 nm, $\Delta z_{NA}$=5917 nm, and the theoretical lateral resolution $\Delta r$ can be calculated to be 778.6 nm. Since $\Delta z_{NA} \gg \Delta z_s \approx \Delta z$, we can see that the coherence length is the limiting factor of the axial resolution. The theoretical axial and lateral resolution values are roughly consistent with the experimental FWHM values shown in FIG. 2(*f*).

It is noteworthy that there are also some PMMA particles within the MIR illumination area that don't show contrast in the photothermal image, which is due to the maximum contrast of the cold image and the photothermal image may not be at the same depth (as shown in FIG. 18). We can see that, the PMMA bead only showing contrast in the cold frame (indicated by the red arrow in FIG. 18) shows the maximum cold and photothermal contrast at different depths. And all the PMMA particles within the MIR illumination area show photothermal contrast in the sum image of different depths (FIG. 18(*d*)).

FIGS. 3($a_1$), 3($a_2$), 3($a_3$), 3($b_1$), 3($b_2$), 3($b_3$), 3($c_1$), 3($c_2$), 3($c_3$), 3($d_1$), 3($d_2$), 3($d_3$), 3($e_1$), 3($e_2$), 3($e_3$), 3($f_1$), 3($f_2$), 3($f_3$), 3($g_1$), 3($g_2$), 3($g_3$), and 3(*h*) illustrate BS-FF-OCT imaging of polypropylene fiber mattress, according to some exemplary embodiments. Specifically, FIGS. 3($a_{1-3}$) illustrates cold wide-field images at different depths. FIGS. 3($b_{1-3}$-$c_{1-3}$) illustrate wide-field MIP images at 1450 cm-1 and 1600 cm-1. 1450 cm-1 is the C—H asymmetric deformation vibration bond in polypropylene, and 1600 cm-1 is at off-resonance. FIGS. 3($d_{1-3}$) illustrate cold FF-OCT images at different depths. FIGS. 3($e_1$-3-$f_{1-3}$) illustrate BS-FF-OCT images at 1450 cm-1 and 1600 cm-1. FIGS. 3($g_{1-3}$) illustrate 3D reconstruction of cold FF-OCT and BS-FF-OCT images. (from a view direction that slightly offsets the direction facing the XY plane) FIG. 3(*h*) illustrates comparison of BS-FF-OCT and FTIR spectrum. The BS-FF-OCT spectrum is extracted from the position in FIG. 3($e_2$) indicated by the green arrow. FTIR spectrum is acquired by a commercial FTIR spectroscopy from a bulky measurement of the polypropylene fiber sample. BS-FF-OCT images and spectrum are normalized by MIR powers. All images are denoised by BM4D algorithm. BS-FF-OCT and FTIR spectrum is smoothed by Gaussian-weighted moving average filter. All intensity values are in linear scales. Image sizes: FIGS. 3(*a-f*) 144 μm (800 pixels)×144 μm (800 pixels), FIGS. 3($g_{1-3}$) 144 μm (800 pixels)×144 μm (800 pixels)×75 μm (75 depths).

To demonstrate the 3D spectroscopic imaging capability of BS-FF-OCT of the current disclosure, polypropylene fiber mattress from a standard surgical mask in air is used as a testbed (FIGS. 3($a_1$), 3($a_2$), 3($a_3$), 3($b_1$), 3($b_2$), 3($b_3$), 3($c_1$), 3($c_2$), 3($c_3$), 3($d_1$), 3($d_2$), 3($d_3$), 3($e_1$), 3($e_2$), 3($e_3$), 3($f_1$), 3($f_2$), 3($f_3$), 3($g_1$), 3($g_2$), 3($g_3$), and 3(*h*)). To emphasize the depth-resolving capability of BS-FF-OCT, which is novel compared to the conventional wide-field MIP, the wide-field cold, on-resonance, and off-resonance MIP images at different depths are captured as shown in FIGS. 3(*a-c*). Those wide-field images are captured at different focus positions, and they are obtained under the same experimental condition and acquisition parameters, except that the reference arm is blocked, which makes a fair comparison to those of BS-FF-OCT. As shown in FIGS. 3(*a-c*), the depth-resolving capability of conventional wide-field MIP imaging is very limited, where the fiber features are indistinguishable. In contrast, BS-FF-OCT images in FIGS. 3(*d-f*) clearly resolve features at different depths. Both wide-field MIP images and BS-FF-OCT images demonstrate bond-selective capability, i.e., at the C—H asymmetric deformation vibration bond at around 1450 $cm^{-1}$. While FIG. 3(*b*) and FIG. 3(*e*) both show bright contrast, no contrast was found at the 1600 $cm^{-1}$ off-resonance wavenumber images (see FIG. 3(*c*) and FIG. 3(*f*)). To further show the 3D imaging capability of BS-FF-OCT, we perform 3D reconstruction of the polypropylene fiber mattress for a total depth range of 75 μm (see FIG. 3(*g*)). We notice that each fiber strip in FIG. 3(*g*) shows "double strips". Since FF-OCT measures back reflections from the sample, the air-polypropylene top and polypropylene-air bottom interfaces of each fiber strip create two distinguishable strips. Also, the diameter of each fiber strip is larger than the axial resolution of the setup thus we can see the two reflection interfaces. FIG. 3(*h*) shows the BS-FF-OCT spectrum extracted from the position indicated by the green arrow in FIG. 3($e_2$) and comparison with the FTIR spectrum. Both BS-FF-OCT and FTIR spectra show peaks for the C—H symmetric deformation vibration bond at around 1370 $cm^{-1}$ and the C—H asymmetric deformation vibration bond at around 1450 $cm^{-1}$. These results further verify the bond-selective capability and demonstrate good spectral fidelity.

FIGS. 4($a_1$), 4($a_2$), 4($a_3$), 4($b_1$), 4($b_2$), 4($b_3$), 4($c_1$), 4($c_2$), 4($c_3$), 4($d_1$), 4($d_2$), 4($d_3$), 4($e_1$), 4($e_2$), 4($e_3$), 4($e_4$), 4($e_5$), and 4($e_6$) illustrate BS-FF-OCT imaging of cancer cell spheroids, according to some exemplary embodiments. Specifically, FIGS. 4($a_{1-3}$) illustrate cold wide-field images at different depths. FIGS. 4($b_{1-3}$) illustrate cold FF-OCT images at different depths. FIGS. 4($c_{1-3}$-$d_{1-3}$) illustrate BS-FF-OCT images at 1650 cm-1, and 1775 cm-1. 1650 cm-1 is the amide I band in protein, and 1775 cm-1 is at off-resonance. FIGS. 4($e_{1-6}$) illustrate cross-sectional images along the dashed lines in FIG. 4($c_2$). BS-FF-OCT images are normalized by MIR powers. All intensity values are in linear scales. Image sizes: FIGS. 4(*a-d*) 72 μm (400 pixels)×72 μm (400 pixels), FIGS. 4($e_{1-6}$) 72 μm (400 pixels)×20 μm (40 depths).

It has been demonstrated that mid-infrared photothermal microscopes are useful tools for biomedical study and disease diagnosis, e.g., imaging the lipid distribution in living cells for cancer diagnosis and imaging the protein secondary structure for Alzheimer's disease diagnosis. As a new technique in the mid-infrared photothermal microscope family, the BS-FF-OCT of the current disclosure also has great application in biomedical imaging applications. Furthermore, compared to other mid-infrared photothermal microscope modalities, BS-FF-OCT has a unique advantage in imaging highly scattering 3D biological samples, benefiting from the implementation of FF-OCT.

To demonstrate the broad application potential of BS-FF-OCT on biological samples, human bladder cancer cell spheroids and *C. elegans* are used as testbeds. FIGS. 4($a_1$), 4($a_2$), 4($a_3$), 4($b_1$), 4($b_2$), 4($b_3$), 4($c_1$), 4($c_2$), 4($c_3$), 4($d_1$), 4($d_2$), 4($d_3$), 4($e_1$), 4($e_2$), 4($e_3$), 4($e_4$), 4($e_5$), and 4($e_6$) show the BS-FF-OCT images of human bladder cell spheroids. The high-density areas (cytoplasm) and low-density areas (nucleus, two examples are indicated by the red dashed line areas in FIG. 4($b_2$)) inside the cell spheroids volume can be seen clearly (see FIG. 4(*b*)). Features from different depths can be distinguished compared to the cold wide-field images in FIG. 4(*a*). FIG. 4(*c*), and FIG. 4(*d*) confirm the bond-selective capability, i.e., at 1650 $cm^{-1}$ (see FIG. 4(*c*)) in resonance with the amide I band of proteins where there is a stronger photothermal contrast than that of at off-resonance 1775 $cm^{-1}$ (see FIG. 4(*d*)). Moreover, the cutting-through sectioning images along the axial direction of the dashed lines in FIG. 4($c_2$) show the cytoplasm and nucleus areas from the side views (see FIG. 4(*e*)).

FIGS. 5($a_1$), 5($a_2$), 5($a_3$), 5($b_1$), 5($b_2$), 5($b_3$), 5($c_1$), 5($c_2$), 5($c_3$), 5($d_1$), 5($d_2$), 5($d_3$), 5($e_1$), 5($e_2$), 5($f_1$), 5($f_2$), 5($g_1$), and 5($g_2$) illustrate BS-FF-OCT imaging of *C. elegans*, according to some exemplary embodiments. Specifically, FIGS. 5($a_{1-3}$) illustrate cold wide-field images at different depths. FIGS. 5($b_{1-3}$) illustrate cold FF-OCT images at different depths. FIGS. 5($c_{1-3}$-$d_{1-3}$) illustrate BS-FF-OCT images at 1650 cm-1, and 1770 cm-1. 1650 cm-1 is the amide I band in protein, and 1770 cm-1 is at off-resonance. FIGS. 5($e_{1-2}$-$g_{1-2}$) illustrate cross-sectional images along the dashed lines in FIG. 5($b_1$), FIG. 5($c_1$), and FIG. 5($d_1$). BS-FF-OCT images are normalized by MIR powers. All intensity values are in linear scales. Image sizes: FIGS. 5($a_{1-3}$-$d_{1-3}$) 108 μm (600 pixels)×108 μm (600 pixels), (e-g) 108 μm (600 pixels)×28 μm (28 depths). The unit of all the color calibration bars is the arbitrary unit (a.u.).

FIGS. 5($a_1$), 5($a_2$), 5($a_3$), 5($b_1$), 5($b_2$), 5($b_3$), 5($c_1$), 5($c_2$), 5($c_3$), 5($d_1$), 5($d_2$), 5($d_3$), 5($e_1$), 5($e_2$), 5($f_1$), 5($f_2$), 5($g_1$), and 5($g_2$) illustrate the BS-FF-OCT images of *C. elegans*. The cold FF-OCT images in FIG. 5($b$) show features inside the *C. elegans* worm at various depths. In contrast, scatterers from different planes hinder these futures in the cold wide-field images due to the lack of optical-sectioning capability (see FIG. 5($a$)). The BS-FF-OCT images in FIG. 5($c$) show strong photothermal contrast at 1650 cm-1, amide I band whereas the photothermal contrast at the 1770 cm-1 off-resonance wavenumber in FIG. 5($d$) is weak. This confirms the chemical selective capability since the *C. elegans* is rich in protein. To further demonstrate the 3D sectioning capability of the BS-FF-OCT setup, the cutting-through sectioning images along the axial direction and dashed lines shown in FIGS. 5($b_1$-$d_1$) are plotted in FIGS. 5($e$-$g$). In these side views, the different structures inside the worm are shown more clearly.

FIGS. 6($a_1$), 6($a_2$), 6($a_3$), 6($b_1$), 6($b_2$), 6($b_3$), 6($c_1$), 6($c_2$), 6($c_3$), 6($d_1$), 6($d_2$), 6($d_3$), 6($e_1$), 6($e_2$), 6($e_3$), 6($f_1$), 6($f_2$), 6($f_3$), and 6($g$) illustrate BS-FF-OCT imaging of myelinated axons in mouse brain tissue, according to some exemplary embodiments. Specifically FIGS. 6($a_{1-3}$) illustrate cold wide-field images at different depths. FIGS. 6($b_{1-3}$) illustrate cold FF-OCT images at different depths. FIGS. 6($c_1$-3-$e_{1-3}$) illustrate BS-FF-OCT images at 1650 cm-1, 1740 cm-1, and 1775 cm-1. 1650 cm-1 is the amide I band in protein, 1740 cm-1 is the C═O band in lipids, and 1775 cm-1 is at off-resonance. FIGS. ($f_{1-3}$) illustrate 3D reconstruction of cold FF-OCT and BS-FF-OCT images. (from a view direction that slightly offsets the direction facing the XY plane). FIG. 6($g$) illustrates the BS-FF-OCT spectrum. The BS-FF-OCT spectrum is extracted from another dataset shown in the additional disclosure material in FIG. 16. BS-FF-OCT Images and spectrum are normalized by MIR powers. All images are denoised by BM4D algorithm. BS-FF-OCT spectrum is smoothed by Gaussian-weighted moving average filter. All intensity values are in linear scales. Image sizes: FIGS. 6($a$-$e$) 144 μm (800 pixels)×144 μm (800 pixels), FIGS. 6($f_{1-3}$) 144 μm (800 pixels)×144 μm (800 pixels)×20 μm (40 depths).

A region containing myelinated axons in a mouse brain tissue slice (FIGS. 6($a_1$), 6($a_2$), 6($a_3$), 6($b_1$), 6($b_2$), 6($b_3$), 6($c_1$), 6($c_2$), 6($c_3$), 6($d_1$), 6($d_2$), 6($d_3$), 6($e_1$), 6($e_2$), 6($e_3$), 6($f_1$), 6($f_2$), 6($f_3$), and 6($g$)) is chosen as the testbed to demonstrate the application potential of our setup for imaging highly scattering biological samples. Martin Schnell et al. Infrared spectroscopic imaging of biological tissues through a Mirau interference objective, where the tissue sample is only 5 μm thick, has been previously demonstrated. In the current disclosure, BS-FF-OCT imaging up to 20 μm depth of the myelinated axons region in a mouse brain tissue is described in detail. The BS-FF-OCT setup can image thicker tissues owing to its particular design. The reference arm is fixed in a prior study, since a Mirau objective is adopted to generate the interference signal. In contrast, BS-FF-OCT according to the current disclosure is based on a time-domain FF-OCT with a separated and tunable reference arm. Thus, in the BS-FF-OCT system setup of the current disclosure, the coherence plane can be tuned to the deeper layers of the samples, as long as there are enough backscattering photons. FIG. 6($a$) shows the cold wide-field reflection images focused at different depths. Due to limited depth-resolving capability, FIG. 6($a$) looks similar at all depths. The photothermal wide-field reflection images focused at different depths shown in FIG. 7 also look similar. In comparison, the cold FF-OCT brain tissue images can distinguish myelinated axon structures from different depths (see FIG. 6($b$)).

Second, an alternative MIR and probe pulse timing configuration is adopted to maximize the detected photothermal signal. Prior simulations demonstrate that photothermal cooling time increases with the sample size (a similar simulation result is also shown in the additional disclosure material in connection with FIG. 15). A suitable heating and probe pulse width and timing configuration is important in photothermal measurement to achieve either thermal confinement or improve the photothermal signal. Because the present technology covers the samples with very different sizes (the smallest, 1 μm PMMA beads, and the very bulky sample, brain tissue with a total thickness of 150 μm), different pulse widths and timing configurations are needed for different samples. Details are included in the additional disclosure material in connection with Table S1. The maximum photothermal signal can be obtained when the temperature difference between the "hot" and "cold" states is largest. Therefore, there should be enough time between the probe pulses to differentiate the "hot" and "cold" states. In the pulse timing configuration shown in FIG. 1($b$), the time window between the first probe pulse for the "cold" state and the last probe pulse for the "hot" state is only 50 μs, which is not enough for the cooling of the 150-μm-thick brain tissue. Thus, a new timing configuration is added to the system setup of the current disclosure, as shown in FIG. 9. The maximum cooling time in this alternative timing configuration is limited to 9 ms by the camera period time (10 ms) and the MIR pulse train width (1 ms). MIR-probe delay scan is also performed, as shown in FIG. 10 and FIG. 11. The cooling time constant of the 150-μm-thick brain tissue is found to be about 1.21 ms, showing that this thick tissue sample indeed requires an alternative timing configuration. Using the optimized MIR-probe delay value (0 ms) shown in FIG. 11($a$), BS-FF-OCT imaging results of myelinated axons of different depths are shown in FIGS. 6($c$-$e$). At the 1650 $cm^{-1}$ Amide I and 1740 $cm^{-1}$ C═O bands, the BS-FF-OCT contrast is strong whereas the images at the 1775 $cm^{-1}$ off-resonance wavenumber have very weak contrast. This result reflects the major chemical content of myelinated axons, i.e., protein and lipids. The 3D reconstruction results of the cold FF-OCT and BS-FF-OCT images at 1650 cm-1 and 1775 $cm^{-1}$ are shown in FIG. 6($f$).

To demonstrate the chemical selectivity, hyperspectral BS-FF-OCT imaging was performed. FIG. 6($g$) shows the BS-FF-OCT spectrum extracted from another dataset shown in the additional disclosure material in connection with FIG. 16. The spectrum shown in FIG. 6($g$) is smoothed to reduce the noise level. The raw spectrum is shown in the supporting information FIG. 8. The peak positions (1550 $cm^{-1}$, 1640

$cm^{-1}$, 1730 $cm^{-1}$) shown in the spectrum are consistent with the peak positions for amide II (1550 $cm^{-1}$), amide I (1650 $cm^{-1}$), and the C═O band (1740 $cm^{-1}$) in protein and lipids, respectively. The other peak shown at 1460 $cm^{-1}$ is altered from the amide II band with the deuterium-oxide-based environment (i.e., the water-based environment is not used due to the MIR absorption of water). The spectrum is consistent with the result in the literature except for the peak at 1460 $cm^{-1}$.

According to the present disclosure, described and illustrated is a 3D chemical imaging technology termed bond-selective full-field optical coherence tomography (BS-FF-OCT). The capability of BS-FF-OCT is demonstrated on polymer samples, including 1-micron PMMA beads and polypropylene fibers, and biological samples, including mouse brain tissue, *C. elegans*, and human bladder cancer cell spheroids. The BS-FF-OCT system setup according to the current disclosure has demonstrated the ability to image up to 20 μm depth of highly scattering biological tissue. It is noteworthy that the main factor that limits the imaging depth is the strong tissue scattering of the visible probe beam, rather than the absorption of the mid-infrared beam. The absorption length of the mid-infrared beam depends on the wavenumber and the sample. For example, the mid-infrared penetration depth on skin tissue can reach 50~ 100 μm, depending on the water content. Since we are using deuterium oxide as the medium to avoid the absorption of the water at 1500 $cm^{-1}$~1750 $cm^{-1}$, the mid-infrared penetration depth could reach at least 100 μm.

Furthermore, the system of the disclosure is capable of imaging highly scattering samples, which is beyond the reach of phase tomography. With BS-FF-OCT of the current disclosure, the high-density areas (cytoplasm) and the low-density areas (nucleus) inside a cell spheroid can be resolved. Compared to other imaging methods, the BS-FF-OCT of the current disclosure has clear advantages. BS-FF-OCT is a label-free method, while prior approaches require fluorescent dye labeling, and it only detects the surface by UV excited fluorescence. Also, compared to some prior approaches, the mid-infrared photothermal approach of the current disclosure benefits from a much larger mid-infrared absorption cross-section of vibrational bonds compared to that of Raman scattering. Also, IR absorption is especially sensitive to fingerprint vibrations, such as the amide I band as a signature of protein secondary structure, while SRS is highly sensitive to high-wavenumber CH vibration. As a result, for myelin sheath, the SRS or CARS signal would predominantly arise from the lipid membrane that is rich in CH bonds. Instead, the photothermal OCT contrast arises from the proteins inside the myelin membrane. This complimentary relationship between Raman and IR opens a lot of opportunities for the reported BS-FF-OCT work. For example, we can potentially use this method to detect the protein secondary structure in brain slices, in which beta-sheet protein aggregate is a signature of neurodegenerative diseases.

Additionally, the full-field mode, which is key to high throughput analysis, is not possible with prior microscopy or the prior scanning scheme of MIP. Compared to the previous scanning MIP, the imaging depth on biology samples of the current disclosure is similar. An advantage of the current technology is that it is not only a 3D IR imaging method but also a wide-field IR imaging method. And the wide-field (full-field) mode is the key to high throughput analysis. The 29 μm depth of view imaging of the cell (only one single cell) in prior work contains only 80*120*29≈0.28 mega voxels, and considering the 1 ms dwell time at each voxel, the acquisition costs about 5 min. While in the current technology, for example, the result of the brain tissue contains 800*800*40≈26 mega voxels, and considering the 8 s acquisition time at each depth, the total acquisition time is also about 5 min. The imaging speed (voxel number/time) is improved by 90 times due to the use of wide-field configuration.

In summary, described herein in detail is a novel and nonobvious bond-selective full-field OCT technique that enables label-free high throughput volumetric spectroscopic imaging at isotropic 1.0-micron resolution, with broad potential applications in biological imaging.

Additional Disclosure Material

The following description and the drawings to which it refers form a part of the present Detailed Description.

Detailed Derivation of the Photothermal Signal Equation.

First, the interference signal between the sample arm and the reference arm is analyzed. Assuming the probe LED source has a uniform spectral density between the wavevector $$k_1 = \frac{2\cdot\pi}{\lambda_1}$$

and wavevector $$k_2 = \frac{2\cdot\pi}{\lambda_2},$$

(where $\lambda_1$=495 nm and $\lambda_2$=595 nm are the lower and upper wavelength bounds of the probe LED source) and assuming the optical path length of the sample arm and the reference arm are $OPL_{sample}$ and $OPL_{reference}$, respectively. Assuming that $E_{sample}$ is the reflected field magnitude from a specific depth of the sample, that $I_{incoherent}$ is the reflection intensity from the sample depths that are not coherent with the reference mirror, that $E_{reference}$ is the reflected light field from the reference mirror. Then the detected interferometric image by the camera can be written by the integration as shown below, $$I_{camera} = \int_{k_1}^{k_2} \frac{I_{incoherent}}{k_2 - k_1} + \frac{E_{sample}\cdot E_{reference}}{k_2 - k_1}\cdot\cos[k\cdot(OPL_{sample} - OPL_{reference})]\,dk \quad \text{(A1)}$$

which can then be written as, $$I_{camera} = I_{incoherent} + E_{sample}\cdot E_{reference}\cdot \Gamma(OPL_{sample} - OPL_{reference})\cdot\cos\left[\frac{k_2+k_1}{2}\cdot(OPL_{sample} - OPL_{reference})\right] \quad \text{(A2)}$$

where $$\Gamma(OPL_{sample} - OPL_{reference}) = \frac{2\sin\left[\frac{k_2-k_1}{2}\cdot(OPL_{sample} - OPL_{reference})\right]}{(k_2-k_1)\cdot(OPL_{sample} - OPL_{reference})},$$

is the coherence function [1]. As shown in FIG. 13, we can see that the $\Gamma(OPL_{sample}-OPL_{reference})$ is a slow-varying term and the $$\cos\left[\frac{k_2+k_1}{2}.(OPL_{sample}-OPL_{reference})\right]$$

is a fast-varying term as functions of $(OPL_{sample}-OPL_{reference})$.

Then, the phase change, $\Delta\varphi$, of the fast-varying term, $$\cos\left[\frac{k_2+k_1}{2}\cdot(OPL_{sample}-OPL_{reference})\right],$$

induced by the piezo stage is discussed. When the piezo stage position changes $\Delta z$, the corresponding phase change is as follows, $$\Delta\varphi=\frac{k_2+k_1}{2}\cdot 2\cdot\Delta z \tag{A3}$$

where the value of $\Delta z$ is set to make $$\Delta\varphi=\frac{\pi}{2}.$$

Since the piezo stage shifts three times, the maximum phase change of the fast-varying term is $$\frac{3\pi}{2},$$

the change of the slow-varying term, the coherence function, can be neglected, as shown in FIG. 13.

Having this phase change equals to $$\frac{\pi}{2},$$

in the "cold" state, assuming $$E_{sample}^{cold}$$

is the reflected field magnitude from a specific depth i of the sample, that $$I_{incoherent}^{cold}$$

is the reflection intensity from the sample depths that are not coherent with the reference mirror, that $$OPL_{sample}^{cold}$$

is the optical path length of the sample, that $OPL_{reference}$ is the optical path length of the reference arm, that $E_{reference}$ is the reflected light field from the reference mirror, and that $$I_1^{cold} \text{ to } I_4^{cold}$$

are the intensity of the four raw images captured by the camera with different phase differences, then $$I_1^{cold} \text{ to } I_4^{cold}$$

can be expressed as follows, $$I_1^{cold}=I_{incoherent}^{cold}+E_{sample}^{cold}\cdot E_{reference}\cdot\Gamma\left(OPL_{sample}^{cold}-OPL_{reference}\right)\cdot\cos\left[\frac{k_2+k_1}{2}\cdot\left(OPL_{sample}^{cold}-OPL_{reference}+0\right)\right] \tag{A4}$$

$$I_2^{cold}=I_{incoherent}^{cold}+E_{sample}^{cold}\cdot E_{reference}\cdot\Gamma\left(OPL_{sample}^{cold}-OPL_{reference}\right)\cdot\cos\left[\frac{k_2+k_1}{2}\cdot\left(OPL_{sample}^{cold}-OPL_{reference}+\frac{\pi}{2}\right)\right] \tag{A5}$$

$$I_3^{cold}=I_{incoherent}^{cold}+E_{sample}^{cold}\cdot E_{reference}\cdot\Gamma\left(OPL_{sample}^{cold}-OPL_{reference}\right)\cdot\cos\left[\frac{k_2+k_1}{2}\cdot\left(OPL_{sample}^{cold}-OPL_{reference}+\pi\right)\right] \tag{A6}$$

$$I_4^{cold}=I_{incoherent}^{cold}+E_{sample}^{cold}\cdot E_{reference}\cdot\Gamma\left(OPL_{sample}^{cold}-OPL_{reference}\right)\cdot\cos\left[\frac{k_2+k_1}{2}\cdot\left(OPL_{sample}^{cold}-OPL_{reference}+\frac{3\pi}{2}\right)\right] \tag{A7}$$

To retrieve $$E_{sample}^{cold},$$

we subtract equation (A1) from (A5) and subtract equation (A6) from (A4), $$I_1^{cold}-I_3^{cold}=E_{sample}^{cold}\cdot E_{reference}\cdot\Gamma\left(OPL_{sample}^{cold}-OPL_{reference}\right)\cdot 2\cdot\cos\left(OPL_{sample}^{cold}-OPL_{reference}\right) \tag{A8}$$

$$I_2^{cold}-I_4^{cold}=E_{sample}^{cold}\cdot E_{reference}\cdot\Gamma\left(OPL_{sample}^{cold}-OPL_{reference}\right)\cdot 2\cdot\left[-\sin\left(OPL_{sample}^{cold}-OPL_{reference}\right)\right] \tag{A9}$$

In equations (A8) and (A9), the incoherent intensity term that is from other depths is canceled but the sin and cos terms still exist. To cancel the sin and cos terms, the square of equations (A8) and (A9) are summed and then square rooted as follows:

$$\sqrt{\left(I_1^{cold}-I_3^{cold}\right)^2+\left(I_2^{cold}-I_4^{cold}\right)^2}=E_{sample}^{cold}\cdot E_{reference}\cdot\Gamma\left(OPL_{sample}^{cold}-OPL_{reference}\right)\cdot 2 \tag{A10}$$

Since the reflected field from the reference mirror is uniform and can be treated as constant, $$E_{sample}^{cold}\cdot\Gamma\left(OPL_{sample}^{cold}-OPL_{reference}\right)$$

can be obtained from equation (A10).

Similarly, in the "hot" state, the reflected field magnitude $$E_{sample}^{hot}\cdot\Gamma\left(OPL_{sample}^{hot}-OPL_{reference}\right)$$

can be obtained by the following equation, $$\sqrt{\left(I_1^{hot}-I_3^{hot}\right)^2+\left(I_2^{hot}-I_4^{hot}\right)^2}=E_{sample}^{hot}\cdot E_{reference}\cdot\Gamma\left(OPL_{sample}^{hot}-OPL_{reference}\right)\cdot 2 \quad (A11)$$

Subtract equation (A11) from (A10), and the detected photothermal FF-OCT image from the sample's depth i, $$I_{photothermal}^{i},$$

can be obtained, $$I_{photothermal}^{i}=\sqrt{\left(I_1^{cold}-I_3^{cold}\right)^2+\left(I_2^{cold}-I_4^{cold}\right)^2}-\sqrt{\left(I_1^{hot}-I_3^{hot}\right)^2+\left(I_2^{hot}-I_4^{hot}\right)^2}=\left[E_{sample}^{cold}\cdot\Gamma\left(OPL_{sample}^{cold}-OPL_{reference}\right)-E_{sample}^{hot}\cdot\Gamma\left(OPL_{sample}^{hot}-OPL_{reference}\right)\right]\cdot E_{reference}\cdot 2 \quad (A12)$$

Equation (A12) describes how a photothermal image of a specific depth of sample can be obtained by using 4 cold raw images and 4 hot raw images. Considering the coherent plane correction made at each depth in the "cold" state, as induced in the previous section, $$OPL_{sample}^{cold}-OPL_{reference}=0,\text{ and }\Gamma\left(OPL_{sample}^{cold}-OPL_{reference}\right)=1,$$

and ignoring the constant term, $E_{reference}\cdot 2$, then equation (A12) can be further written as follows, $$I_{photothermal}^{i}=\left(E_{sample}^{cold}-E_{sample}^{hot}\right)+E_{sample}^{hot}\cdot\left[1-\Gamma\left(OPL_{sample}^{cold}-OPL_{sample}^{hot}\right)\right] \quad (A13)$$

Then let $$E_{sample}^{cold}-E_{sample}^{hot}=\Delta E_{sample},$$

which is the reflection change induced by the photothermal effect at the sample's depth i, and let $$OPL_{sample}^{cold}-OPL_{sample}^{hot}=\Delta OPL_{sample},$$

which is the optical path length change induced by the photothermal effect for all the upper layers of the samples depth i. Noticing $\Delta E_{sample}$ and $[1-\Gamma(\Delta OPL_{sample})]$ are both small terms and ignoring their product (as the product is a second-order small term), then we can obtain, $$I_{photothermal}^{i}=\Delta E_{sample}+E_{sample}^{cold}\cdot[1-\Gamma(\Delta OPL_{sample})] \quad (A14)$$

FIGS. 7($a_1$), 7($a_2$), 7($a_3$), 7($b_1$), 7($b_2$), 7($b_3$), 7($c_1$), 7($c_2$), and 7($c_3$) include widefield MIP images of myelinated axons in mouse brain tissue shown in FIGS. 6($a_1$), 6($a_2$), 6($a_3$), 6($b_1$), 6($b_2$), 6($b_3$), 6($c_1$), 6($c_2$), 6($c_3$), 6($d_1$), 6($d_2$), 6($d_3$), 6($e_1$), 6($e_2$), 6($e_3$), 6($f_1$), 6($f_2$), and 6($f_3$), according to some exemplary embodiments.

FIG. 8 includes a raw BS-FF-OCT spectrum and a smoothed BS-FF-OCT spectrum of myelinated axons in mouse brain tissue in FIG. 6(*g*), according to some exemplary embodiments.

FIG. 9 includes alternative timing configuration of the probe, MIR pulses, and camera of the system of the disclosure, according to some exemplary embodiments. In some exemplary embodiments, an optical chopper blade (for example, Thorlabs, MC1F10A) with tunable duty cycle is used to modulate the MIR pulses.

FIGS. 10(*a*), 10(*b*), 10(*c*), 10(*d*), 10(*e*), 10(*f*), 10(*g*), and 10(*h*) illustrate BS-FF-OCT imaging of myelinated axons in mouse brain tissue with different probe MIR pulse delay time, according to some exemplary embodiments. FIGS. 10(*a*), 10(*b*), 10(*c*), 10(*d*), 10(*e*), 10(*f*), 10(*g*), and 10(*h*) illustrated BS-FF-OCT images with delay time ($t_d$) of 0, 0.5, 1, . . . , 3.5 ms.

FIG. 11 illustrates the BS-FF-OCT signal for different probe MIR pulse delay times, according to some exemplary embodiments. The BS-FF-OCT signal value is extracted from the dashed area shown in FIG. 10(*d*). Exponential fitting of the cooling time (after 0 ms) of the sample. The fitting value of the cooling time constant is 1.214 ms. The definition of delay is the time from the end of the IR pulse train and the beginning of the probe pulse.

FIGS. 12(*a*), 12(*b*), and 12(*c*) illustrate coherence plane correction for automatic volumetric image acquisition, according to some exemplary embodiments. FIG. 12(*a*) illustrates the coherence plane position at old focus. FIG. 12(*b*) illustrates shifted coherence plane position at new focus. FIG. 12(*c*) Illustrates corrected coherence plane position at new position.

FIGS. 13(*a*), 13(*b*), 13(*c*), 13(*d*), 13(*e*), and 13(*f*) illustrate coherence function plotting illustration, according to some exemplary embodiments. FIG. 13(*a*) illustrates the coherence function plotting, $$\frac{2\sin\left[\frac{k_2-k_1}{2}\cdot(OPL_{sample}-OPL_{reference})\right]}{(k_2-k_1)\cdot(OPL_{sample}-OPL_{reference})}.$$

FIG. 13(*b*) illustrates the fast-varying term, $$\cos\left[\frac{k_2+k_1}{2}\cdot(OPL_{sample}-OPL_{reference})\right].$$

FIG. 13(*c*) illustrates the multiplying result of FIGS. 13(*a*) and 13(*b*). FIGS. 13(*d-f*) Illustrate corresponding images of FIGS. (a-c) using sample depth as the variable and assuming the reference mirror is at a fixed position. The FWHM of FIG. 13(*d*) shows the coherence length.

FIGS. 14(*a*) and 14(*b*) illustrate illumination area characterization, according to some exemplary embodiments. FIG. 14(*a*) illustrates the illumination area of the probe beam. The whole field of view of the camera is illuminated by the probe beam. FIG. 14(*b*) illustrates the illumination area of the MIR heating beam and contour plotting of the fitting result using a 2D Gaussian function. $I(x,y)=Ce^{-x_2/A_2-y_2/B_2}$. The fitting is performed by fitting the photothermal signal intensity of the beads at different locations. The fitting result: A=39.2 μm, B=76.3 μm. The corresponding FWHMs: 65 μm, 127 μm. The image is a z projection of all the depths from the uncropped raw data of FIGS. 2(*a*1), 2(*a*2), 2(*a*3), 2(*b*1), 2(*b*2), 2(*b*3), 2(*c*1), 2(*c*2), 2(*c*3), 2(*d*1), 2(*d*2), 2(*d*3), 2(*e*1), 2(*e*2), 2(*e*3), 2(*f*1), 2(*f*2), and 2(*f*3).

FIGS. 15(*a*), 15(*b*), and 15(*c*) illustrate a temperature cooling profile COMSOL simulation of different size PMMA beads, according to some exemplary embodiments. FIG. 15(*a*) illustrates the temperature cooling profile of a 1 μm PMMA bead in water environment. FIG. 15(*b*) illustrates the temperature cooling profile of a 10 μm PMMA bead in water environment. FIG. 15(*c*) illustrates the temperature cooling profile of a 50 μm PMMA bead in water environment. The fitting result of the cooling time constant of FIGS. 15(*a*), 15(*b*), and 15(*c*) are 0.23 μs, 15.32μ, and 681.42 μs, respectively.

FIGS. 16(*a*1), 16(*a*2), 16(*a*3), 16(*b*1), 16(*b*2), 16(*b*3), 16(*c*1), 16(*c*2), 16(*c*3), 16(*d*1), 16(*d*2), 16(*d*3), 16(*e*1), 16(*e*2), 16(*e*3), 16(*f*1), 16(*f*2), 16(*f*3), and 16(*g*) illustrate BS-FF-OCT imaging of myelinated axons in mouse brain tissue, according to some exemplary embodiments. FIG. 16(*a*) illustrates cold widefield images at different depths. FIG. 16(*b*) illustrates cold FF-OCT images at different depths. FIGS. 16(*c-e*) illustrate BS-FF-OCT images at 1650 cm-1, 1740 cm-1, and 1775 cm-1. 1650 cm-1 is the amide I band in protein, 1740 cm-1 is the C═O band in lipids, and 1775 cm-1 is at off-resonance. FIG. 16(*f*) illustrates 3D reconstruction of cold FF-OCT and BS-FF-OCT images. FIG. 16(*g*) illustrates BS-FF-OCT spectrum. The BS-FF-OCT spectrum is extracted from another dataset shown in the support information. BS-FF-OCT Images and spectrum are normalized by MIR powers. All images are denoised by BM4D algorithm. BS-FF-OCT spectrum is smoothed by Gaussian-weighted moving average filter. All intensity values are in linear scales.

FIGS. 17(*a*) and 17(*b*) illustrate theoretical calculations of the coherence functions of both cold and hot states, according to some exemplary embodiments. FIG. 17(*a*) Illustrates coherence functions of both cold (blue curve) and hot (orange curve) states. FIG. 17(*b*) illustrates zoom-in view of FIG. 17(*a*) with indicators of the 4 cold (black star) raw image is assumed to be 0.1 measurements and the 4 hot (red star) raw image measurements.

$$\frac{\Delta E_{sample}}{E_{sample}^{cold}}$$

is assumed to be 0.1 and $\Delta OPL_{sample}$ is assumed to be 0.2.

FIGS. 18(*a*3), 18(*b*3), 18(*c*), 18(*d*), and 18(*e*) illustrate the BS-FF-OCT signal of PMMA beads in agargel gel, according to some exemplary embodiments. FIGS. 18($a_3$) and 18(*b*3) illustrate original images from FIGS. 2(*a*1), 2(*a*2), 2(*a*3), 2(*b*1), 2(*b*2), 2(*b*3), 2(*c*1), 2(*c*2), 2(*c*3), 2(*d*1), 2(*d*2), 2(*d*3), 2(*e*1), 2(*e*2), 2(*e*3), 2(*f*1), 2(*f*2), and 2(*f*3) with a red arrow indicating a PMMA bead only showing contrast in panel FIG. 18(*a*3) not showing contrast in panel FIG. 18(*b*3). FIGS. 18(*c-d*) illustrate sum of the images from depth 8 μm, 8.5 μm, and 9 μm. FIG. 18(*e*) illustrate 1-D cross line profile of the PMMA bead indicated by the red arrow.

TABLE 1

Detail of all the parameters of the probe and MIR pulses.

| 1. | | Pulse Timing Configuration | MIR modulation (50 Hz) | MIR pulse width (ns) | MIR power attenuation method | MIR average power | MIR-probe delay | Probe modulation | Probe pulse width (μs) | Probe average power (mW) |
|---|---|---|---|---|---|---|---|---|---|---|
| 2. | FIG. 2 | FIG. 1b | 50% | 50 | 2 silicon chips | 66 mW @ 1730 cm$^{-1}$ | 0 μs | No modulation (20 kHz) | 1.2 | 3.1 |
| 3. | FIG. 3 | FIG. 1b | 10% | 50 | ND1 + 1 silicon chip | 0.1 mW @ 1450 cm$^{-1}$ | | 50 pulses on, 150 pulses off (20 kHz) | 2.6 | 1.7 |
| 4. | FIG. 4 | FIG. 1b | 10% | 50 | 2 silicon chips | 1 mW @ 1650 cm$^{-1}$ | 0 μs | 50 pulses on, 150 pulses off (20 kHz) | 4.8 | 3.1 |
| 5. | FIG. 5 | FIG. 1b | 50% | 50 | 3 silicon chips | 3.3 mW @ 1650 cm$^{-1}$ | 0 μs | No modulation (20 kHz) | 1.2 | 3.1 |
| 6. | FIG. 6 | FIG. S3 | 5% | 50 | ND1 | 0.1 mW @ 1650 cm$^{-1}$ | 0 ms | No modulation (100 kHz) | 260 | 3.4 |

ND1: IR Reflective Neutral Density Filter, OD: 1.0. (NDIR10B, Thorlabs)

Silicon chip: about 50% transmission rate @ 1450 cm$^{-1}$. (Item #775, Silicon 100 mm P/B (100) 1-10 ohm-cm 500 um DSP Prime, University Wafer)

The repetition rate of MIR pulse without modulation is 20 kHz (baseband frequency).

The MIR-probe delay is measured by the time of the end (defined by reaching (1-1/e) of the maximum) of the rising edge of the probe pulse subtracts that of the end of the MIR pulse or pulse train.

The invention claimed is:

1. A wide-field bond-selective optical coherence tomography (OCT) system for imaging a sample, comprising:

a source of infrared light for generating infrared light, wherein an intensity of infrared light is modulated between an on state and an off state, the infrared light being directed onto the sample, during the on state, to selectively heat the sample to a hot state associated with a first temperature, and the sample being allowed to cool, during the off state, to a cold state associated with a second temperature;

a source of probe light for generating probe light, the probe light being directed onto the sample;

a first objective in a reference arm of the wide-field bond-selective OCT system;

a second objective in a sample arm of the wide-field bond-selective OCT system;

a first actuator for providing sample depth scanning with respect to the first objective by actuating a reference mirror and a second actuator for providing sample depth scanning with respect to the second objective by actuating the sample, wherein the first and second actuators are synchronized for automatic coherence and focal plane matching; and a detection system for receiving scattered probe light reflected from the sample, which allows detection of the hot state or the cold state of the sample, wherein the time period of the off state, predetermined based on the sample, allows for the difference between the first temperature and the second temperature to be the largest, such that the hot and cold states of the sample are differentiable by the detection system.

2. The wide-field bond-selective OCT system of claim 1, wherein the source of probe light comprises a light-emitting diode (LED).

3. The wide-field bond-selective OCT system of claim 1, wherein the detection system comprises a camera.

4. The wide-field bond-selective OCT system of claim 3, wherein the camera is a CCD camera.

5. The wide-field bond-selective OCT system of claim 3, wherein the camera is a CMOS camera.

6. The wide-field bond-selective OCT system of claim 1, wherein the infrared light is pulsed.

7. The wide-field bond-selective OCT system of claim 1, wherein the infrared light is mid-infrared (MIR) light.

8. The wide-field bond-selective OCT system of claim 1, further comprising a movable stage for providing controllable movement for scanning the sample.

9. A wide-field bond-selective optical coherence tomography (OCT) method for imaging a sample, comprising:

generating infrared light, and directing the infrared light onto the sample, wherein an intensity of infrared light is modulated between an on state and an off state, the infrared light being directed to selectively heat the sample to a hot state associated with a first temperature, and the sample being allowed to cool, during the off state, to a cold state associated with a second temperature;

generating probe light and directing the probe light onto the sample;

providing a first objective in a reference arm of the wide-field bond-selective OCT system;

providing a second objective in a sample arm of the wide-field bond-selective OCT system;

actuating a reference mirror in the reference arm and the sample in the sample arm to provide sample depth scanning with automated and synchronized coherence and focal plane matching;

receiving scattered probe light reflected from the sample with a detection system; and detecting a change in received probe light that is indicative of absorption of infrared light from the sample, thereby allowing detection of a hot state or a cold state of the sample, wherein the time period of off state, predetermined based on the sample, allows for the difference between the first temperature and the second temperature to be the largest, such that the hot and cold states of the sample are differentiable by the detection system.

10. The wide-field bond-selective OCT method of claim 9, wherein the probe light is generated by a light-emitting diode (LED).

11. The wide-field bond-selective OCT method of claim 9, wherein the scattered probe light reflected from the sample is received by a camera.

12. The wide-field bond-selective OCT method of claim 11, wherein the camera is a CCD camera.

13. The wide-field bond-selective OCT method of claim 11, wherein the camera is a CMOS camera.

14. The wide-field bond-selective OCT method of claim 11, wherein the camera acquires images of received scattered probe light from the sample while an intensity of infrared light to the sample is modulated.

15. The wide-field bond-selective OCT method of claim 9, wherein the infrared light is pulsed.

16. The wide-field bond-selective OCT method of claim 9, wherein the infrared light is mid-infrared (MIR) light.

17. The wide-field bond-selective OCT method of claim 9, further comprising providing controllable movement for scanning the sample.

18. The wide-field bond-selective OCT method of claim 9, further comprising the step of creating a three-dimensional reconstruction of infrared absorbing regions within the sample.

19. The wide-field bond-selective OCT method of claim 9, wherein the probe light is modulated between an on state and an off state and is synchronized with the modulation of the intensity of infrared light, such that the probe light enters an on state when the sample heats up to the first temperature and when the sample cools down to the second temperature.

20. The wide-field bond-selective OCT method of claim 9, further comprising repeating the receiving and detecting steps at a plurality of relative phases between the sample and reference arms.

21. The wide-field bond-selective OCT method of claim 9, further comprising repeating the receiving and detecting steps at a plurality of wavelengths of the infrared source.

22. The wide-field bond-selective OCT method of claim 9, further comprising the step of producing a bond-selective 3D sectioned image of the sample.

23. The wide-field bond-selective OCT method of claim 9, wherein the sample is a biological tissue section.

24. The wide-field bond-selective OCT method of claim 23, wherein the sample has a thickness of greater than 5 micrometers.

25. The wide-field bond-selective OCT method of claim 9, further comprising repeating the receiving and detecting steps at a plurality of sample depths.

26. The wide-field bond-selective OCT method of claim 9, wherein the sample depth scanning has a range of at least 10 micrometers.

27. The wide-field bond-selective OCT method of claim 9, further comprising reconstructing a 3D chemical image of the sample.

28. The wide-field bond-selective OCT method of claim 9, wherein the sample is highly scattering.

* * * * *